US012774309B2

(12) United States Patent
Martinez et al.

(10) Patent No.: US 12,774,309 B2
(45) Date of Patent: Oct. 27, 2026

(54) TREATMENT OF HEPATIC AND CARDIOVASCULAR DISORDERS

(71) Applicants: LIFESEARCH, Toulouse (FR); INSTITUT NATIONAL DE LA SANTE ET DE LA RECHERCHE MEDICALE (INSERM), Paris (FR); UNIVERSITÉ PAUL SABATIER TOULOUSE III, Toulouse (FR)

(72) Inventors: Laurent Martinez, Toulouse (FR); Souad Najib, Saint-Leon (FR); Nabil Sioufi, Los Angeles, CA (US)

(73) Assignees: LIFESEARCH, Toulouse (FR); LIFESEARCH INSTITUT NATIONAL DE LA SANTE ET DE LA RECHERCHE MEDICALE (INSERM), Paris (FR); UNIVERSITÉ PAUL SABATIER TOULOUSE III, Toulouse (FR)

( * ) Notice: Subject to any disclaimer, the term of this patent is extended or adjusted under 35 U.S.C. 154(b) by 1164 days.

(21) Appl. No.: 17/786,124

(22) PCT Filed: Dec. 18, 2020

(86) PCT No.: PCT/EP2020/087211

§ 371 (c)(1),
(2) Date: Jun. 16, 2022

(87) PCT Pub. No.: WO2021/123300

PCT Pub. Date: Jun. 24, 2021

(65) Prior Publication Data

US 2023/0050846 A1 Feb. 16, 2023

(30) Foreign Application Priority Data

Dec. 20, 2019 (EP) .................................... 19306743

(51) Int. Cl.

| | |
|---|---|
| ***C07K 14/47*** | (2006.01) |
| ***A61K 47/54*** | (2017.01) |
| ***A61K 47/60*** | (2017.01) |
| ***A61P 1/16*** | (2006.01) |
| ***C12N 15/63*** | (2006.01) |

(52) U.S. Cl.

CPC ........ *C07K 14/4702* (2013.01); *A61K 47/542* (2017.08); *A61K 47/60* (2017.08); *A61P 1/16* (2018.01); *C12N 15/63* (2013.01)

(58) Field of Classification Search

None

See application file for complete search history.

(56) References Cited

U.S. PATENT DOCUMENTS

| | | | | |
|---|---|---|---|---|
| 2004/0156843 | A1 | 8/2004 | Papathanassiu | |
| 2015/0065556 | A1* | 3/2015 | Birsoy | G01N 33/6896 435/6.12 |
| 2022/0347113 | A1* | 11/2022 | Du | C07K 14/4722 |

FOREIGN PATENT DOCUMENTS

| | | | |
|---|---|---|---|
| WO | 02068680 | A2 | 9/2002 |
| WO | 02068680 | A3 | 9/2002 |
| WO | 2004087904 | A1 | 10/2004 |
| WO | 2012101142 | A1 | 8/2012 |
| WO | 2018169282 | A2 | 9/2018 |
| WO | 2018169282 | A3 | 9/2018 |

OTHER PUBLICATIONS

Genbank Accession AAH04955, ATPIF1 protein [*Homo sapiens*], Oct. 3, 2003.*

GenBank Accession NP_001124626, ATPase inhibitor, mitochondrial precursor [Pongo abelii]., Nov. 11, 2018.*

Bowie et al., Deciphering the Message in Protein Sequences: Tolerance to Amino Acid Substitutions, Science, 1990, vol. 247, issue 4948, pp. 1306-1310.*

International Search Report and Written Opinion for International Application No. PCT/EP2020/087211 mailed on Apr. 1, 2021, 12 pages.

Duparc et al., "Serum level of HDL particles are independently associated with long-term prognosis in patients with coronary artery disease: The Genes study", Scientific Reports, 2020, vol. 10, No. 1, 8138, 12 pages.

Genoux et al., "Mitochondrial Inhibitory Factor 1 (IF1) is Present in Human Serum and is Positively Correlated with HDL-Cholesterol", PLoS ONE, 2011, vol. 6, No. 9, e23949, 8 pages.

Rouslin et al., "ATPase activity, IF1 Content, and Proton Conductivity of ESMP from Control and Ischemic Slow and Fast Heart-Rate Hearts", Journal of Bioenergetics and Biomembranes, 1995, vol. 27, No. 4, pp. 459-466.

* cited by examiner

*Primary Examiner* — Benjamin P Blumel

(74) *Attorney, Agent, or Firm* — MH2 Technology Law Group, LLP

(57) ABSTRACT

The present invention relates to a peptide and its use as a medicament, in particular in the treatment of metabolic syndrome, non-alcoholic fatty liver disease (NAFLD), cardiovascular disease (CVD) or cholestatic liver disease.

13 Claims, 13 Drawing Sheets

Specification includes a Sequence Listing.

A Formula I

B Formula II

C Formula III

D Formula IV

E Fmoc-K-[palmitoyl ]-OH

A

B

SEQUENCE LISTING

```
<160> NUMBER OF SEQ ID NOS: 5

<210> SEQ ID NO 1
<211> LENGTH: 31
<212> TYPE: PRT
<213> ORGANISM: Artificial Sequence
<220> FEATURE:
```

-continued

<223> OTHER INFORMATION: Peptide according the invention

<400> SEQUENCE: 1

Arg Gly Ala Gly Ser Ile Arg Glu Ala Gly Gly Ala Phe Gly Lys Arg
1 5 10 15

Glu Gln Ala Glu Glu Glu Arg Tyr Phe Arg Ala Gln Ser Arg Glu
20 25 30

<210> SEQ ID NO 2
<211> LENGTH: 31
<212> TYPE: PRT
<213> ORGANISM: Artificial Sequence
<220> FEATURE:
<223> OTHER INFORMATION: Scramble peptide

<400> SEQUENCE: 2

Gly Glu Ala Lys Ser Tyr Ala Glu Lys Gly Glu Ala Arg Gly Glu Arg
1 5 10 15

Gly Thr Lys Gly Glu Phe Arg Ile Phe Lys Arg Glu Ala Thr Asp
20 25 30

<210> SEQ ID NO 3
<211> LENGTH: 8
<212> TYPE: PRT
<213> ORGANISM: Artificial Sequence
<220> FEATURE:
<223> OTHER INFORMATION: Signature peptide 1

<400> SEQUENCE: 3

Glu Ala Gly Gly Ala Phe Gly Lys
1 5

<210> SEQ ID NO 4
<211> LENGTH: 7
<212> TYPE: PRT
<213> ORGANISM: Artificial Sequence
<220> FEATURE:
<223> OTHER INFORMATION: Signature peptide

<400> SEQUENCE: 4

Glu Ala Gly Gly Ala Phe Gly
1 5

<210> SEQ ID NO 5
<211> LENGTH: 81
<212> TYPE: PRT
<213> ORGANISM: Homo sapiens

<400> SEQUENCE: 5

Gly Ser Asp Gln Ser Glu Asn Val Asp Arg Gly Ala Gly Ser Ile Arg
1 5 10 15

Glu Ala Gly Gly Ala Phe Gly Lys Arg Glu Gln Ala Glu Glu Glu Arg
20 25 30

Tyr Phe Arg Ala Gln Ser Arg Glu Gln Leu Ala Ala Leu Lys Lys His
35 40 45

His Glu Glu Glu Ile Val His His Lys Lys Glu Ile Glu Arg Leu Gln
50 55 60

Lys Glu Ile Glu Arg His Lys Gln Lys Ile Lys Met Leu Lys His Asp
65 70 75 80

Asp

TREATMENT OF HEPATIC AND CARDIOVASCULAR DISORDERS

CROSS REFERENCE TO RELATED APPLICATIONS

This application is a U.S. National Stage Application of PCT/EP2020/087211 filed 18 Dec. 2020, which claims priority to European Patent Application No. 19306743.6 filed on 20 Dec. 2019, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 16 Jun. 2022, is named 0177_0191_ST25.txt and is 3 kilobytes in size.

BACKGROUND OF THE INVENTION

Metabolic syndrome is a clustering of at least three of the five following medical conditions: central obesity, high blood pressure, high blood sugar, high serum triglycerides, and low serum high-density lipoprotein (HDL).

According to the American Heart Association, metabolic syndrome occurs when a person has three or more of the following measurements:

- Abdominal obesity (Waist circumference of greater than 40 inches in men, and greater than 35 inches in women).
- Triglyceride level of 150 milligrams per deciliter of blood (mg/dL) or greater.
- HDL cholesterol of less than 40 mg/dL in men or less than 50 mg/dL in women.
- Systolic blood pressure (top number) of 130 millimeters of mercury (mm Hg) or greater, or diastolic blood pressure (bottom number) of 85 mm Hg or greater.
- Fasting glucose of 100 mg/dL or greater.

Metabolic syndrome is associated with the risk of developing cardiovascular disease (CVD), type 2 diabetes and/or fatty liver, such as non-alcoholic fatty liver disease (NAFLD).

NAFLD generally refers to a spectrum of hepatic lipid disorders characterized by hepatic fat accumulation (steatosis) in people who drink little or no alcohol. NAFLD is also defined as a progressive liver disease that ranges from hepatic fat accumulation (simple steatosis) to non-alcoholic steatohepatitis (NASH).

NASH is a progressive disease of the liver characterized histologically by hepatic lipid accumulation, hepatocyte damage and inflammation resembling alcoholic hepatitis. NASH is a critical stage in the process that can lead to advanced fibrosis (also called "NASH associated fibrosis"), cirrhosis, liver failure and/or HCC (Hepatocellular Carninoma). A careful history of a lack of significant alcohol intake is essential to establish this diagnostic. NASH is one of the most common causes of elevated aminotransferases in patients referred for evaluation to hepatologists. NASH is generally associated with energy metabolism pathologies, including obesity, dyslipidemia, diabetes and metabolic syndrome.

NASH is the hepatic expression of the metabolic syndrome.

Extensive dysregulation of hepatic cholesterol homeostasis drives progressive hepatic inflammation and fibrosis and has been documented in NASH. This dysregulation occurs at multiple levels including decreased cholesterol excretion in bile, either as cholesterol or as bile acids [13].

It is therefore believed that the cholesterol circulating level plays an important role in the metabolic syndrome, in particular the dyslipidemia pattern in this syndrome.

Cholesterol circulating in the human body is carried by plasma lipoproteins, which are particles of complex lipid and protein composition that transport lipids in the blood. Two types of plasma lipoproteins that carry cholesterol are low density lipoproteins ("LDL") and high density lipoproteins ("HDL"). LDL particles are believed to be responsible for the delivery of cholesterol from the liver (where it is synthesized or obtained from dietary sources) to extrahepatic tissues in the body. HDL particles, on the other hand, are believed to aid in the transport of cholesterol from the extrahepatic tissues to the liver, where the cholesterol is catabolized and eliminated. Such transport of cholesterol from the extrahepatic tissues to the liver is referred to as "reverse cholesterol transport".

The reverse cholesterol transport ("RCT") pathway is a multistep process which involves: (i) HDL-mediated efflux, i.e. the initial removal of cholesterol from various pools of peripheral cells; (ii) cholesterol esterification by the action of lecithin:cholesterol acyltransferase ("LCAT"), thereby preventing a reentry of effluxed cholesterol into cells, (iii) HDL endocytosis by hepatocytes and (iv) excretion of cholesterol from HDL into the bile, either directly of after conversion into bile acids.

The RCT pathway is mediated by HDL particles. A pathway for HDL endocytosis in the liver involving "cell surface F1Fo-ATPase" (also known as "ecto F1Fo-ATPase") and the P2Y13 receptor that regulates HDL-cholesterol removal was described in [1]. The presence of a nucleotidase activity of F1-ATPase subunit (hereafter "F1-ATPase activity") at the cell surface of hepatocytes (hereafter "ecto-F1-ATPase activity"), allowing the hydrolysis of ATP to ADP, which in turn stimulates the P2Y13 receptor activities resulting in the uptake of the HDL by the cells was described in [2]. Reference [3] and [14] confirmed the relationship between P2Y13 receptor and the reverse cholesterol transport and atherogenesis in mice.

At the cell surface of endothelial cells, F1-ATPase activity hydrolyzes extracellular ATP into ADP, which in turn stimulates the P2Y1 receptor activities resulting in nitric oxide production by endothelial nitric oxide synthase (eNOS) and promoting signaling survival pathways [15] [5].

According to the above, F1-ATPase activators are a promising therapeutic class for treating metabolic syndrome, cardiovascular disease (CVD), non-alcoholic fatty liver disease (NAFLD) or cholestatic liver disease.

Apolipoprotein A-I (apoA-I) is known to be a F1-ATPase activator [1]. ApoA-I binding to cell surface F1Fo-ATPase stimulates its ATPase activity (F1-ATPase activity), which generates extracellular adenosine diphosphate (ADP), a process that is prevented by the F1-ATPase inhibitor named Inhibitory Factor 1 (IF1) [1]. It has been shown that apoA-I and its mimetics have excellent potential to be useful clinically for the treatment of metabolic syndrome, such as cardiovascular disease (CVD) [4]. However, even if clinical proof of principle has been already established, apoA-I and its mimetics have never reached the drug status.

There is therefore a need to identify new F1-ATPase activators that can be used as a medicament, in particular for the treatment of metabolic syndrome, cardiovascular disease (CVD), non-alcoholic fatty liver disease (NAFLD) or cholestatic liver disease.

SUMMARY OF THE INVENTION

The inventors have surprisingly found that the peptide 10-40 of mature human IF1 (SEQ ID NO: 1) is a F1-ATPase activator that can be used as a medicament, in particular for the treatment of metabolic syndrome, cardiovascular disease (CVD), non-alcoholic fatty liver disease (NAFLD) or cholestatic liver disease.

The present invention therefore relates to a peptide comprising a peptide having at least 70% sequence identity to the amino acid sequence of SEQ ID NO: 1 (RGAGSIREAGGAFGKREQAEEERYFRAQSRE), wherein said peptide is a F1-ATPase activator.

The invention also relates to a pharmaceutical composition comprising a therapeutically active amount of a peptide according to the invention and a pharmaceutically acceptable vehicle or carrier.

The invention also relates to a peptide according to the invention or a pharmaceutical composition according to the invention for use as a medicament, in particular for use in the treatment of metabolic syndrome, non-alcoholic fatty liver disease (NAFLD), cardiovascular disease (CVD) or cholestatic liver disease.

The invention also relates to a nucleotide sequence encoding a peptide according to the invention, a vector comprising a nucleotide sequence according to the invention and a cell comprising a nucleotide sequence according to the invention.

DETAILED DESCRIPTION OF THE INVENTION

Definitions

Unless defined otherwise, all technical and scientific terms used herein have the same meaning as commonly understood by those of ordinary skill in the art to which the invention belongs.

The articles "a", "an" and "the" are used herein to refer to one or to more than one (i.e., to at least one) of the grammatical object of the article.

Reference throughout this specification to "one embodiment", "an embodiment", "a particular embodiment", "a certain embodiment", "an additional embodiment", "a further embodiment" or combinations thereof means that a particular feature, structure or characteristic described in connection with the embodiment is included in at least one embodiment of the present invention.

The term "peptide" refers to an amino acid sequence, i.e. a chain of amino acids linked by peptide bonds, and may include modification(s), for example, glycosylation(s), acetylation(s), phosphorylation(s), amidation(s), N- and/or C-terminal modification(s), as well as other modification(s) known in the art to increase the stability of the peptide, its in vivo half-life and/or its cell permeability, compared to a peptide devoid of said modifications. Said modification(s) may be for example, at least one covalent attachment of the peptide with at least one long-lasting molecule, for example in N- or C-terminal.

The term "amino acid" as used herein is meant to include both natural and synthetic amino acids, and both D and L amino acids.

For the purposes of the present invention, the "identity" or "homology" is calculated by comparing two aligned sequences in a comparison window. The alignment of the sequences makes it possible to determine the number of positions (nucleotides or amino acids) common to the two sequences in the comparison window. The number of common positions is then divided by the total number of positions in the comparison window and multiplied by 100 to obtain the percentage of homology. The determination of the percentage of sequence identity can be done manually or by using well-known computer programs. In a particular embodiment of the invention, the identity or the homology corresponds to 1 to 8 substitutions, for example 1, 2, 3, 4, 5, 6, 7 or 8 substitutions of an amino acid residue. Preferably, the at least one substitution is a conservative amino acid substitution. By "conservative amino acid substitution", it is meant that an amino acid can be replaced with another amino acid having a similar side chain. Families of amino acid having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "long-lasting molecule" means a molecule that can be attached to a peptide and that increase the in vivo half-life of said peptide, compared to a peptide not attached to said long-lasting molecule. In particular, the in vivo half-life of the peptide attached to the long-lasting molecule is at least 2 times higher compared to the in vivo half-life of said peptide not attached to said long-lasting molecule, preferably at least 5 times higher, for example at least 10 times higher, for example at least 20 times higher. According to the invention, the long-lasting molecule may be a fatty acid, albumin, polyethylene glycol (PEG) and/or the Fc portion of immunoglobulin G.

The term "fatty acid" according to the invention refers to a carboxylic acid consisting of a hydrocarbon chain and a terminal carboxyl group, especially any of those occurring as esters in fats and oils. According to the invention, the fatty acid improves the half-life of the peptide. In one aspect, the fatty acid is palmitic acid. In another aspect, the fatty acid includes, but is not limited to, pentadecylic acid, margaric acid, stearic acid, nonadecylic acid, arachidic acid, heneicosylic acid, behenic acid, tricosylic acid, lignoceric acid, pentacosylic acid, ω-carboxypentadecanoyl (C16-diacid), ω-carboxyheptadecanoyl (C18-diacid) or any other saturated fatty acid. In yet another aspect, the fatty acid includes, but is not limited to, linoleic acid, arachidonic acid, stearidonic acid, palmitoleic acid, vaccenic acid, paullinic acid, oleic acid, or any other unsaturated fatty acid.

The term "albumin" means the blood plasma protein produced in the liver and forming a large proportion of all plasma protein, such as the human serum albumin (HSA, CAS Number: 70024-90-7).

The term "polyethylene glycol" or "PEG" refers to any water soluble poly(ethylene glycol) or poly(ethylene oxide). The expression PEG will comprise the structure $-(CH_2CH_2O)_n-$, where n is an integer from 2 to about 1000. A commonly used PEG is end-capped PEG, wherein one end of the PEG termini is end-capped with a relatively inactive group such as alkoxy, while the other end is a hydroxyl group that may be further modified by linker moieties. An often used capping group is methoxy and the corresponding end-capped PEG is often denoted mPEG. Hence, mPEG is $CH_3O(CH_2CH_2O)_n-$, where n is an integer from 2 to about 1000 sufficient to give the average molecular weight indicated for the whole PEG moiety, e.g.

for mPEG Mw 2,000, n is approximately 44 (a number that is subject for batch-to-batch variation). The notion PEG is often used instead of mPEG. "PEG" followed by a number (not being a subscript) indicates a PEG moiety with the approximate molecular weight equal the number. Hence, "PEG2000" is a PEG moiety having an approximate molecular weight of 2000.

The term "Fc portion of immunoglobulin G" refers to a paired set of antibody heavy chain domains, each of which has a $C_H2$ fused to a $C_H3$, which form a structure of about 50 kDa.

The term "pharmaceutically acceptable" means approved by a regulatory agency of the Federal or a state government or listed in the U.S. or European Pharmacopeia or other generally recognized pharmacopeia for use in animals, and humans.

A "pharmaceutical composition" means a composition comprising pharmaceutically acceptable carrier. For example, a carrier can be a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers include starch, glucose, lactose, sucrose, sodium stearate, glycerol monostearate, talc, sodium chloride, dried skim milk, glycerol, propylene glycol, water, ethanol and the like. When the pharmaceutical composition is adapted for oral administration, the tablets or capsules can be prepared by conventional means with pharmaceutically acceptable carriers such as binding agents (e.g. pregelatinized maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

The term "vector" is used herein to refer to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like. According to the invention, the vector may be an expression vector.

The term "expression vector" refers to a vector comprising a polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g. naked or contained in liposomes) and viruses that incorporate the polynucleotide.

An "effective amount" or "therapeutically effective amount" of a compound is that amount of compound which is sufficient to provide a beneficial effect to the subject to which the compound is administered.

The term "administering" includes administration of a peptide or composition of the invention by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary or rectal means, preferably intravenously.

The term "subject", "patient" or "individual", as used herein, refers to a human or non-human mammal (such as a rodent (mouse, rat), a feline, a canine, or a primate) affected or likely to be affected with metabolic syndrome, non-alcoholic fatty liver disease (NAFLD), cardiovascular disease (CVD) or cholestatic liver disease. Preferably, the subject is a human, man or woman.

The term "treating" or "treatment" means reversing, alleviating, inhibiting the progress of, or preventing the disorder or condition to which such term applies, or one or more symptoms of such disorder or condition.

Peptide and Composition

The invention relates to a peptide comprising a peptide having at least 70%, such as at least 71%, at least 72%, at least 73%, at least 74%, at least 75%, at least 76%, at least 77%, at least 78%, at least 79%, for example at least 80%, such as at least 81%, at least 82%, at least 83%, at least 84%, at least 85%, at least 86%, at least 87%, at least 88%, at least 89%, for example at least 90%, such as at least 91%, at least 92%, at least 93%, at least 94%, at least 95%, at least 96%, at least 97%, at least 98%, at least 99% or 100% sequence identity to the amino acid sequence of SEQ ID NO: 1. Accordingly, the invention relates to a peptide comprising a peptide having 1 to 8 substitutions, for example 1, 2, 3, 4, 5, 6, 7 or 8 substitutions of an amino acid residue compared to the amino acid sequence of SEQ ID NO: 1.

The peptide of the invention is a F1-ATPase activator. Activation of F1-ATPase can be measured as detailed in the examples. The F1-ATPase may be the human F1-ATPase or a non-human mammal F1-ATPase (such as a rodent (mouse, rat), a feline, a canine, or a primate). Preferably, the peptide of the invention is a human F1-ATPase activator.

In some embodiments, the peptide of the invention is a peptide having at least 70%, such as at least 71%, at least 72%, at least 73%, at least 74%, at least 75%, at least 76%, at least 77%, at least 78%, at least 79%, for example at least 80%, such as at least 81%, at least 82%, at least 83%, at least 84%, at least 85%, at least 86%, at least 87%, at least 88%, at least 89%, for example at least 90%, such as at least 91%, at least 92%, at least 93%, at least 94%, at least 95%, at least 96%, at least 97%, at least 98%, at least 99% or 100% sequence identity to the amino acid sequence of SEQ ID NO: 1. Accordingly, the invention relates to a peptide having 1 to 8 substitutions, for example 1, 2, 3, 4, 5, 6, 7 or 8 substitutions of an amino acid residue compared to the amino acid sequence of SEQ ID NO: 1.

The peptide according to the invention may be modified in N-terminal, in C-terminal and/or with internal modifications in order to increase stability, efficacy and/or the half-life of said peptide. N-terminal modifications may be for example acetylation, biotinylation, dansylation, 2, 4-Dinitrophenylation and/or attachment of a long-lasting molecule. C-terminal modifications may be for example amidation and/or attachment of a long-lasting molecule. Internal modifications may be cysteine carbamidomethylation, amino acid substitution, amino acid replacement to aminoisobutyric acid (Aib), phosphorylation and/or attachment of a long-lasting molecule. The peptide may comprise one or more modifications.

In one embodiment, the peptide according to the invention has a N-terminal acetylation. N-terminal acetylation removes the positive charge on the N-terminal of peptides. This modification increases peptide stability by preventing N-terminal degradation.

In another embodiment, the peptide according to the invention has a C-terminal amidation, i.e. the C-terminal of the peptide is synthesized as an amide to neutralize negative charge created by the C-terminal COOH. This modification is added to prevent enzyme degradation.

Thus, the present invention encompasses a peptide having a N-terminal acetylation and a C-terminal amidation, i.e. the peptide of the invention has the following formula: $CH_3CO$-[peptide comprising a peptide having at least 70% sequence identity to the amino acid sequence of SEQ ID NO: 1]-$NH_2$.

In a specific embodiment, the peptide of the invention may have the following formula: $CH_3CO$-[peptide having at least 70% sequence identity to the amino acid sequence of SEQ ID NO: 1]-$NH_2$. Thus, the peptide of the invention may have the following formula $CH_3CO$-[peptide having 1 to 8 substitutions compared to the amino acid sequence of SEQ ID NO: 1]-$NH_2$.

In a preferred embodiment, the peptide of the invention has the following formula:

$CH_3CO$-[peptide comprising a peptide having the sequence SEQ ID NO: 1]-$NH_2$ (I).

In a particularly preferred embodiment, when the peptide of the invention is a peptide having the amino acid sequence of SEQ ID NO: 1, the peptide of the invention has the following formula (I):

$CH_3CO$-[SEQ ID NO: 1]-$NH_2$ (I).

The formula (I) is represented in FIG. 1A.

In another embodiment, the peptide according to the invention is modified by attaching at least one long-lasting molecule at one or more amino acid residues of the amino acid sequence, said long-lasting molecule being selected from the group consisting of albumin, albumin-binding small molecules (such as myristic acid, naphthalene acylsulfonamide, diphenylcyclohexanol phosphate ester and 6-(4-(4-iodophenyl) butanamido) hexanoate), fatty acid, fatty di-acid, Fc portion of immunoglobulin G, polyethylene glycol (PEG), natural polymers such as polysialic acid (PSA or hydroxyethyl starch (HES), recombinant PEG mimetics based on long unstructured peptides such as homo-amino-acid polymer (HAP) composed of Gly4Ser repeats and polypeptide XTEN. The attachment of the long-lasting molecule to the peptide thereby increases the serum half-life of said peptide. An amino acid and/or a linker such as 2-aminoethoxy-2ethoxyacetyl (AEEA) and oligoethylene glycol (OEG) linkers may be inserted between SEQ ID NO: 1 and the long-lasting molecule to avoid steric hindrance.

In some embodiments, the peptide of the invention is modified by attaching at least one long-lasting molecule at the C-terminus of the amino acid sequence. Said long lasting molecule may be attached directly at the C-terminus of the amino acid sequence or through a linker. The linker is preferably one or more amino acid, for example from one to ten amino acids, such as from one to five amino acids, that connects the peptide to the long-lasting molecule. In some embodiments, the linker is one amino acid, such as Alanine (A) or Lysine (K).

Attachment of PEG to a peptide is called PEGylation. Short bifunctional PEG (Poly (ethylene glycol)) can be used as a spacer in bioconjugation of peptides with other molecules. PEG bioconjugation is used to improve proteolytic stability, biodistribution and solubility of the peptide. Techniques of PEGylation are well detailed in the prior art, e.g. in [18].

In a particular embodiment, long-lasting molecule is a fatty acid molecule, such as a palmitic acid. In particular, the peptide of the invention is modified by attaching at least one fatty acid molecule at one or more amino acid residues of the amino acid sequence, preferably the peptide is modified by attaching one fatty acid molecule, such as a palmitic acid, at the C-terminus of the amino acid sequence.

Palmitic acid (also called "palmitoyl" in the present description, in particular in the formulas) is a 16-carbon fatty acid having the formula:

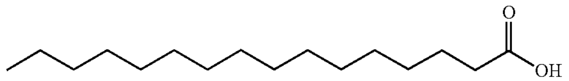 [SMILES: CCCCCCCCCCCCCCCC(=O)O]

Palmitic acid is conjugated to the peptide of the invention to increase its cell permeability and help binding of the peptide to cell membrane.

The fatty acid may be attached to the peptide of the invention via chemical cycloaddition. In one aspect, this chemical cycloaddition comprises copper-catalyzed alkyne-azide cycloaddition. In another aspect, the cycloaddition includes, but is not limited to, transition metal-catalyzed or mediated [5+1] cycloadditions, formal [3+3]cycloaddition, and cycloreversion.

In a preferred embodiment, a fatty acid is attached directly at the C-terminus of the amino acid sequence or through a linker. The linker is preferably one or more amino acid, for example from one to ten amino acids, such as one to five amino acids, that connects the peptide to the long-lasting molecule. In some embodiments, the linker is one amino acid, such as Alanine (A or Ala) or Lysine (K or Lys).

Thus, the present invention encompasses a peptide having the following formula: $CH_3CO$-[peptide comprising a peptide having at least 70% sequence identity to the amino acid sequence of SEQ ID NO: 1]-K-[palmitoyl]-$NH_2$, such as the following formula $CH_3CO$-[peptide having at least 70% sequence identity to the amino acid sequence of SEQ ID NO: 1]-K-[palmitoyl]-$NH_2$. In a preferred embodiment, the peptide of the invention has the formula $CH_3CO$-[peptide comprising a peptide having the sequence SEQ ID NO: 1]-K-[palmitoyl]-$NH_2$, such as the peptide of formula (II):

$CH_3CO$-[SEQ ID NO: 1]-K-[palmitoyl]-$NH_2$ (II).

The formula (II) is represented in FIG. 1B.

In the present description, the term "at least 70% sequence identity" encompasses "at least 70%, such as at least 71%, at least 72%, at least 73%, at least 74%, at least 75%, at least 76%, at least 77%, at least 78%, at least 79%, for example at least 80%, such as at least 81%, at least 82%, at least 83%, at least 84%, at least 85%, at least 86%, at least 87%, at least 88%, at least 89%, for example at least 90%, such as at least 91%, at least 92%, at least 93%, at least 94%, at least 95%, at least 96%, at least 97%, at least 98%, at least 99% or 100% sequence identity".

The present invention also relates to a pharmaceutical composition comprising a therapeutically active amount of a peptide according to the invention and a pharmaceutically acceptable vehicle or carrier.

Therapeutic Use

The invention relates to a peptide according to the invention or a pharmaceutical composition according to the invention for use as a medicament, in particular for use in the treatment of metabolic syndrome, non-alcoholic fatty liver disease (NAFLD), cardiovascular disease (CVD) or cholestatic liver disease.

Non-limiting examples of metabolic syndrome, cardiovascular disease (CVD), non-alcoholic fatty liver disease (NAFLD) or cholestatic liver disease that are treatable by administering a peptide of the invention or a composition thereof include:

(i) a metabolic syndrome, including a disorder of lipoprotein metabolism, dyslipoproteinemia, lipoprotein overproduction or deficiency, elevation of total cholesterol, elevation of low density lipoprotein concentration, elevation of triglyceride concentration, diminution of high density lipoprotein cholesterol, lipid elimination in bile and feces, phospholipid elimination in bile and feces, oxysterol elimination in bile and feces, bile acids elimination in bile and feces, and peroxisome proliferator activated receptor-associated disorders;

(ii) a metabolic syndrome, including a disorder of glucose metabolism, insulin resistance, impaired glucose tolerance, impaired fasting glucose levels in blood, diabetes mellitus, lipodystrophy, central obesity, peripheral lipoatrophy, diabetic nephropathy, diabetic retinopathy, renal disease, and septicemia;

(iii) a cardiovascular disease or a related vascular disorder, including hypertension, coronary artery disease, myocardial infarction, stroke, arrhythmia, atrial fibrillation, heart valve disease, heart failure, cardiomyopathy, pericarditis and impotence;

(iv) a non-alcoholic fatty liver disease (NAFLD), including hepatic steatosis and non-alcoholic steatohepatitis (NASH);

(v) a cholestatic liver disease, including primary biliary cholangitis (PBC, previously known as primary biliary cirrhosis) and primary sclerosing cholangitis (PSC).

As used herein, the term "a disorder of lipoprotein metabolism" means "dyslipidemia". Dyslipidemia include but is not limited to hyperlipidemia and low blood levels of high density lipoprotein (HDL) cholesterol. Thus, the peptide according to the invention or the composition thereof may also alter lipid metabolism in a subject, e.g. increasing HDL cholesterol and/or HDL particle number in the blood of a subject, reducing LDL in the blood of a subject, improving HDL metabolism, improving HDL functions in a subject, reducing free triglycerides in the blood of a subject and/or increasing the ratio of HDL to LDL in the blood of a subject.

As used herein, the term "disorder of glucose metabolism" or "glucose metabolism disorders" involves aberrant glucose storage and/or utilization. To the extent that one or more indicia of glucose metabolism (i.e., blood insulin, blood glucose) are abnormally high, the peptide of the invention or the composition thereof is administered to a subject to restore normal levels. Conversely, to the extent that one or more indicia of glucose metabolism are abnormally low, the peptide of the invention or the composition thereof is administered to a subject to restore normal levels. Normal indicia of glucose metabolism are well known to those of skill in the art. Glucose metabolism disorders include but are not limited to: impaired glucose tolerance; diabetic retinopathy, diabetic nephropathy, insulin resistance; insulin resistance related cancer, such as breast, colon or prostate cancer; diabetes, including but not limited to non-insulin dependent diabetes mellitus (NIDDM), insulin dependent diabetes mellitus (IDDM), gestational diabetes mellitus (GDM), and maturity onset diabetes of the young (MODY); pancreatitis; hypertension; polycystic ovarian disease; and high levels of blood insulin or glucose, or both.

As used herein, the term "cardiovascular disease" or "CVD" refers to a disease of the heart or circulatory system. Cardiovascular disease can be associated with dyslipoproteinemia or dyslipidemia, or both. Cardiovascular diseases include but are not limited to arteriosclerosis; atherosclerosis; stroke; ischemia; perivascular disease (PVD); transient ischemic attack (TIA), fulgurant atherosclerosis; organ graft atherosclerosis; endothelium dysfunctions, in particular those dysfunctions affecting blood vessel elasticity; peripheral vascular disease; coronary heart disease; myocardial infarction; cerebral infarction and restenosis. Non-limiting examples of symptoms of cardiovascular disease include angina, shortness of breath, dizziness, nausea, fatigue, irregular heartbeat, and impotence. In some embodiments, treatment of a cardiovascular disease treats one or more symptoms of cardiovascular disease. In some embodiments, treatment of cardiovascular disease treats impotence.

In a preferred embodiment, NAFLD is non-alcoholic steatohepatitis (NASH)

The peptide of the invention and the pharmaceutical composition thereof may be administered by any convenient route, for example, orally, by intravenous infusion or bolus injection, by absorption through epithelial or mucocutaneous linings (e.g. oral mucosa, rectal and intestinal mucosa, etc.) and can be administered together with another biologically active agent. Administration can be systemic or local. Various delivery systems are known, e.g. encapsulation in liposomes, microparticles, microcapsules, capsules, etc., and can be used to administer a peptide of the invention. In certain embodiments, more than one peptide of the invention is administered to a subject. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration can be left to the discretion of the practitioner, and depends in-part upon the site of the medical condition. In most instances, administration results in the release of the compounds of the invention into the bloodstream.

Pulmonary administration may also be employed, e.g. by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

Advantageously, the peptide or the pharmaceutical composition according to the invention is administered intravenously or subcutaneously.

According to the way of administration, the dosage form will be adapted. The skilled person knows how to adapt the dosage forms that lend themselves to the chosen route of administration. For example, for oral administration, the dosage form may be selected from tablets, including orodispersible tablets, capsules, drink or syrup. For pulmonary administration, the dosage form may be in the form of spray or inhalation products. For intravenous administration, the dosage form may be a sterile solution for injection.

The peptide or the pharmaceutical composition according to the invention may be administered in one or more doses. The dose administered to the subject in need thereof will vary based on several factors including, without limitation, the route of administration, the disease treated or the subject's age. One skilled in the art can readily determine, based on its knowledge in this field, the dosage range required based on these factors and others.

The amount of a peptide of the invention that is effective in the treatment of a particular disease disclosed herein can depend on the nature of the disease, and can be determined by standard clinical techniques. In vitro or in vivo assays can be employed to help identify optimal dosage ranges. The precise dose to be employed in the compositions can also depend on the route of administration or the severity of the Condition, and can be decided according to the judgment of the practitioner and each subject's circumstances.

Other Objects of the Invention

The invention relates to a nucleotide sequence encoding a peptide comprising a peptide having at least 70%, such as at least 71%, at least 72%, at least 73%, at least 74%, at least 75%, at least 76%, at least 77%, at least 78%, at least 79%, for example at least 80%, such as at least 81%, at least 82%, at least 83%, at least 84%, at least 85%, at least 86%, at least 87%, at least 88%, at least 89%, for example at least 90%, such as at least 91%, at least 92%, at least 93%, at least 94%, at least 95%, at least 96%, at least 97%, at least 98%, at least 99% or 100% sequence identity to the amino acid sequence of SEQ ID NO: 1.

In some embodiments, the invention relates to a nucleotide sequence encoding a peptide having at least 70%, such as at least 71%, at least 72%, at least 73%, at least 74%, at least 75%, at least 76%, at least 77%, at least 78%, at least 79%, for example at least 80%, such as at least 81%, at least 82%, at least 83%, at least 84%, at least 85%, at least 86%, at least 87%, at least 88%, at least 89%, for example at least 90%, such as at least 91%, at least 92%, at least 93%, at least 94%, at least 95%, at least 96%, at least 97%, at least 98%, at least 99% or 100% sequence identity to the amino acid sequence of SEQ ID NO: 1.

The nucleotide sequence may be a ribonucleic acid (RNA) sequence or a deoxyribonucleic acid (DNA) sequence, preferably the nucleotide sequence is a DNA sequence. The nucleotide sequence may comprise one or more intron(s) to increase the stability of the corresponding RNAs. The choice of the intron(s) and its positioning in the nucleotide sequence is within the abilities of those skilled in the art. Advantageously, the nucleotide sequence coding for the peptide according to the invention is optimized to improve the translation efficiency of said peptide. The optimization of a nucleotide sequence does not present any particular obstacle for a person skilled in the art who can easily implement the teaching of the prior art.

The invention also relates to a vector comprising a nucleotide sequence according to the invention. Preferably, the vector is an expression vector for expressing the peptide comprising a peptide having at least 70%, such as at least 71%, at least 72%, at least 73%, at least 74%, at least 75%, at least 76%, at least 77%, at least 78%, at least 79%, for example at least 80%, such as at least 81%, at least 82%, at least 83%, at least 84%, at least 85%, at least 86%, at least 87%, at least 88%, at least 89%, for example at least 90%, such as at least 91%, at least 92%, at least 93%, at least 94%, at least 95%, at least 96%, at least 97%, at least 98%, at least 99% or 100% sequence identity to the amino acid sequence of SEQ ID NO: 1. In some embodiments, the vector is an expression vector for expressing the peptide having at least 70%, such as at least 71%, at least 72%, at least 73%, at least 74%, at least 75%, at least 76%, at least 77%, at least 78%, at least 79%, for example at least 80%, such as at least 81%, at least 82%, at least 83%, at least 84%, at least 85%, at least 86%, at least 87%, at least 88%, at least 89%, for example at least 90%, such as at least 91%, at least 92%, at least 93%, at least 94%, at least 95%, at least 96%, at least 97%, at least 98%, at least 99% or 100% sequence identity to the amino acid sequence of SEQ ID NO: 1.

The invention also relates to a cell (host cell) comprising a nucleotide sequence according to the invention or a vector according to the invention. In particular, the cell according to the invention has been transfected, infected or transformed by a nucleotide sequence and/or a vector according to the invention.

Any transfection method well known to those skilled in the art can be used to prepare a cell according to the invention, for example lipofection or calcium phosphate cell transfection or electroporation.

For the purposes of the invention, the term "transformation" means the introduction of a nucleotide sequence into a host cell, so that the host cell is capable of expressing the nucleotide sequence introduced to produce the desired peptide. In particular, the host cell according to the invention is capable of expressing the peptide of the invention.

Examples of host cells include, but are not limited to, prokaryotic cells (such as bacteria) and eukaryotic cells (such as yeast cells, mammalian cells, insect cells, plant cells, etc.). Specific examples include *E. coli, Kluyveromyces* or *Saccharomyces*, mammalian cell lines (e.g. Vero, CHO, 3T3, BHK, COS, Huh-7, HEK, etc.) as well as primary or established mammalian cell cultures (e.g. lymphoblasts, fibroblasts, embryonic cells, epithelial cells, nerve cells, adipocytes, etc.). Cell lines such as SP2/O-Agl4 (ATCC CRL1581), P3X63-Ag8.653 (ATCC CRL1580), CHO DHFR, YB2/0 (ATCC CRL1662) or Huh-7 (ATCC CCL-185) may also be mentioned. It may also be a stem cell taken from a patient, for example a mesenchymal cell. Stem cells can in particular be used in gene therapy or in cell therapy, either autologous or heterologous.

The nucleic sequence, the vector or the cell according to the invention may be used as a medicament, such as for treating the diseases disclosed above in the section "Therapeutic use".

Method of Treatment

The invention related to a method for treating metabolic syndrome, non-alcoholic fatty liver disease (NAFLD), cardiovascular disease (CVD) or cholestatic liver disease comprising administering a peptide according to the invention or a pharmaceutical composition according to the invention to a subject.

Specific embodiments of the method of treatment are derived from the description above.

The invention is further defined by reference to the following examples.

EXAMPLES

Example 1: Preparation of the Peptides

The following peptides were produced by BachemAG (Bubendorf, Switzerland) with >90% purity in acetate salts and dissolved in Phosphate-Buffered Saline (PBS) solution before use:

Formula (I): $CH_3CO$-[SEQ ID NO: 1]-$NH_2$, hereafter called "peptide of formula (I)" or "formula (I)" (represented in FIG. 1A);

Formula (II): $CH_3CO$-[SEQ ID NO: 1]-K-[palmitoyl]-$NH_2$, hereafter called "peptide of formula (II)" or "formula (II)" (represented in FIG. 1B);

SEQ ID No 2: GEAKSYAEKGEARGERGTKGE-FRIFKREATD

Formula (III): $CH_3CO$-[SEQ ID NO: 2]-$NH_2$, hereafter called "Scramble peptide" or "SCR" (represented in FIG. 1C); and Formula (IV): $CH_3CO$-[SEQ ID NO: 2]-K-[palmitoyl]-$NH_2$, hereafter called "Scramble peptide K-C16" or "SCR-K-C16" (represented in FIG. 1D).

Figure 1:
FIG. 1 represents the formula of Fmoc-Lys-[palmitoyl]-OH and formulas (I), (II), (III) and (IV).
Figure 1:
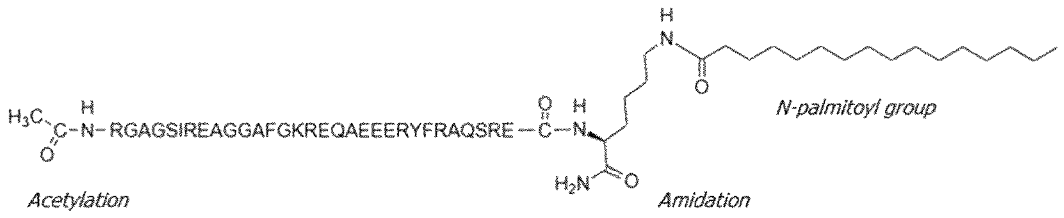
Figure 1:
Figure 1:
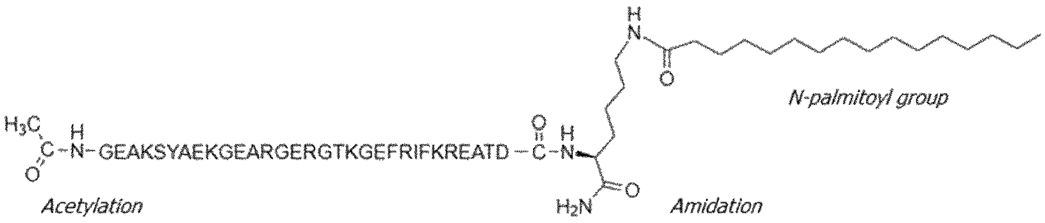
Figure 1:
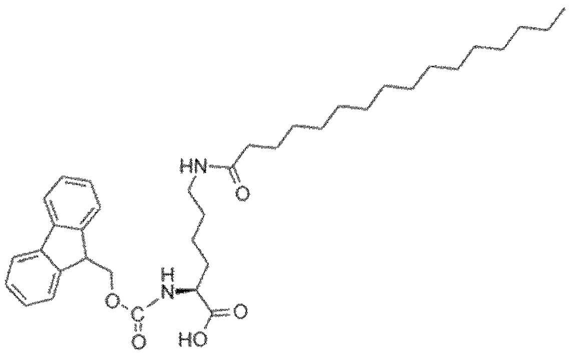

The palmitic acid was introduced via coupling the preformed derivative Fmoc-K-[palmitoyl]-OH (represented in FIG. 1E).

Other labeled and unlabeled peptides SEQ ID NO: 3 (EAGGAFGK) and SEQ ID NO: 4 (EAGGAFG-[$^{13}C_6$, $^{15}N_4$]-K) were purchased from ThermoFisher Scientific with >90% purity and dissolved at 1 mM in 50% acetonitrile.

Example 2: Surface Plasmon Resonance Analysis of the Interaction of the Peptide of Formula (I) and the Peptide of Formula (II) with Human F1Fo-ATPase

Materials and Methods

Surface plasmon resonance (SPR) assays. Binding studies based on SPR technology were performed on a BIAcore T200 optical biosensor instrument (GE Healthcare®, Uppsala, Sweden). The peptide of formula (I) with C-terminal 6×His-tag (Formula (I)-His-tag: $CH_3CO$-[SEQ ID NO: 1]-HHHHHH) and the peptide of formula (II) with C-terminal biotin (Formula (II)-Biotin: $CH_3CO$-[SEQ ID NO: 1]-K-[palmitoyl]-AEEAc-K-[biotinyl]-$NH_2$) were custom-synthesized by BACHEM AG (Bubendorf, Switzerland) with >90% purity in trifluoroacetate salt. Human F1Fo-ATPase was purified from HepG2 cells by immunocapture using mouse monoclonal anti-ATP synthase antibody (12F4AD8AF8, #ab109867, Abcam) according to manufacturer's instructions.

Immobilization of the peptide of formula (I)-6His-tag was performed on a nitrilotriacetic acid (NTA) sensorchip in HBS-P+ buffer (10 mM Hepes pH 7.4, 150 mM NaCl, and 0.05% surfactant P20) (GE Healthcare). To saturate the NTA surface with $Ni_2^+$, flow cells (Fc) were loaded with 0.5 mM $NiCl_2$ solution. The channel Fc1 was left empty and used as a reference surface for nonspecific binding measurements. Formula (I)-6×His was injected in the channel Fc2 at a flow-rate of 5 μL/min and stabilized by amine coupling (Laboratory guideline 29-0057-17 AB). The total amount of immobilized Formula (I)-His-tag was 300-350 resonance units (RU): final concentration 25 μg/mL.

Immobilization of C-term biotinylated peptide of Formula (II)-biotin was performed on streptavidin-coated (SA) sensor chip in HBS-EP buffer (10 mM HEPES [pH 7.4], 150 mM NaCl, 3 mM EDTA, 0.005% surfactant P20) (GE Healthcare). The channel Fc1 was left empty and used as a reference surface for nonspecific binding measurements. Formula (II)-biotin was injected in the channel Fc2 at a flow-rate of 5 μL/min. The total amount of immobilized Formula (II)-biotin was 350-380 RU: final concentration 100 ng/mL. For binding analyses, the F1F0 analyte (584 KDa) was injected sequentially over the immobilized peptides with increased concentrations ranging (3.125 nM-6.25 nM-12.5 nM-25 nM-50 nM) in a single cycle without regeneration of the sensorship between injections. A single-cycle kinetic (SCK) analysis allowed to determine association, dissociation, and affinity constants (Ka, Kd, and $K_D$, respectively). Binding parameters were obtained by fitting the overlaid sensorgrams either with the 1:1 Langmuir binding model or with Steady State Constant Rmax model in the BIAevaluation software version 3.0.

Results

Figure 2:
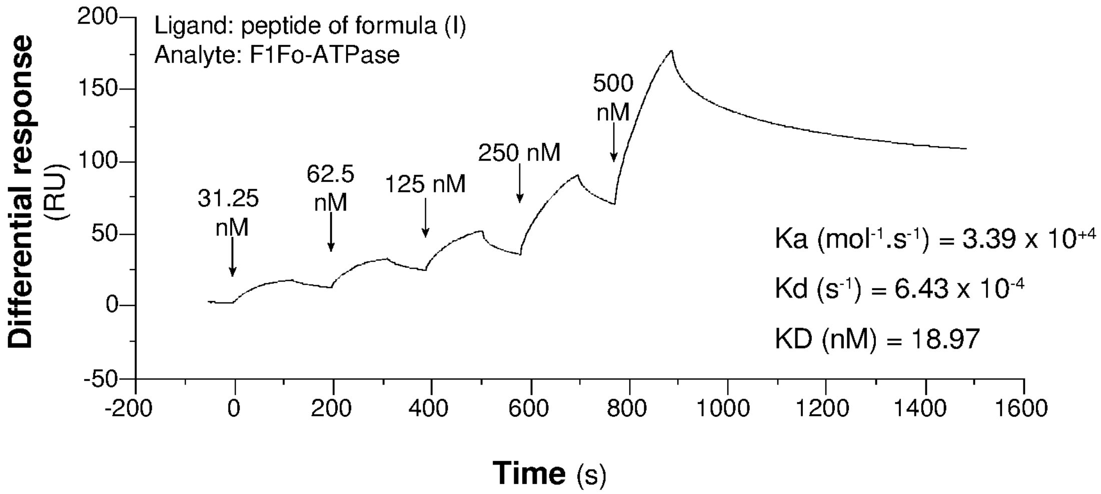
FIG. 2 represents the surface plasmon resonance analysis of the interaction of the peptide of formula (I) and the peptide of formula (II) with purified human FiFo-ATPase. Dose-dependent binding of the human $F_1$Fo-ATPase, used as an analyte, to the peptide of formula (I) (A) and the peptide of formula (II) (B) immobilized on the sensor chip is shown. All sensorgrams represent the RU as a function of time.
Figure 2:
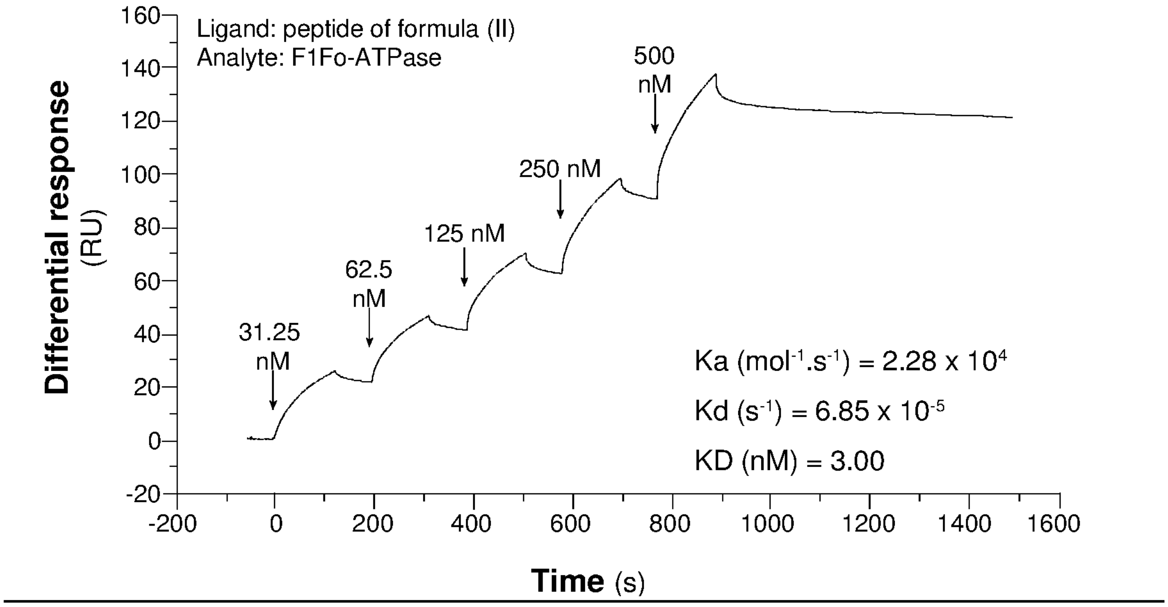

The results are shown in FIG. 2. The sensorgrams in FIG. 2 show a direct interaction between the purified c-ATPase, used as an analyte, and the peptide of formula (I) (FIG. 2A) and the peptide of formula (II) (FIG. 2B) coated on the BIAcore sensor chip. Binding of F1Fo-ATPase to the immobilized peptide of formula (I) and peptide of formula (II) was dose-dependent (31.25 nM-500 nM) allowing us to determine the affinity between the multisubunit complex and the peptide of formula (I) ($K_D$=18.97 nM) and the peptide of formula (II) ($K_D$=4.45 nM)

Conclusion

A direct high affinity interaction was measured between F1Fo-ATPase and the peptide of formula (I), and between F1Fo-ATPase and the peptide of formula (II).

Example 3: Effect of Peptide of Formula (I) and Peptide of Formula (II) on the F1-ATPase Activity Materials and Methods F1-ATPase Activity Assay.

The mature human IF1 protein (SEQ ID NO: 5) was chemically synthesized by GenScript (Piscataway, NJ, USA) at >80% purity. The peptides derived from the mature human IF1 sequence (IF1-1-60, IF1-10-56, IF1-10-47) were produced by BachemAG (Bubendorf, Switzerland) with >90% purity.

Human F1Fo-ATPase was purified from HepG2 cells by immunocapture using mouse monoclonal anti-ATP synthase antibody (12F4AD8AF8, #ab109867, Abcam) according to manufacturer's instructions.

Measurement of F1-ATPase activity was assayed as previously described [20]. Briefly, 10 μg of F1Fo-ATPase was prepared into 50 μL of activity assay buffer (10 mM HEPES, 150 mM NaCl, 5 mM KCl, 5 mM MgCl2, 0.5 mM phosphoenolpyruvate, 250 μM NADH, 100 μM ATP, 20 U lactate dehydrogenase, 120 U pyruvate kinase). The mixture was incubated at 37° C. for 30 min. Then the F1-ATPase activity was measured in a 96-well microplate by adding 5 μL of the mixture (1 μg of F1Fo-ATPase per point) per well to 200 μL of activity assay buffer at 37° C., and by adding 5 μL of buffer with or without peptide (1 μM each). The reduction in the absorbance of NADH was measured at 340 nm for 5 min with a Varioskan™ Flash Multimode Reader (Thermo Fisher Scientific). A slope was calculated for each well and the results expressed as a percentage of the control slope.

Results

Figure 3:
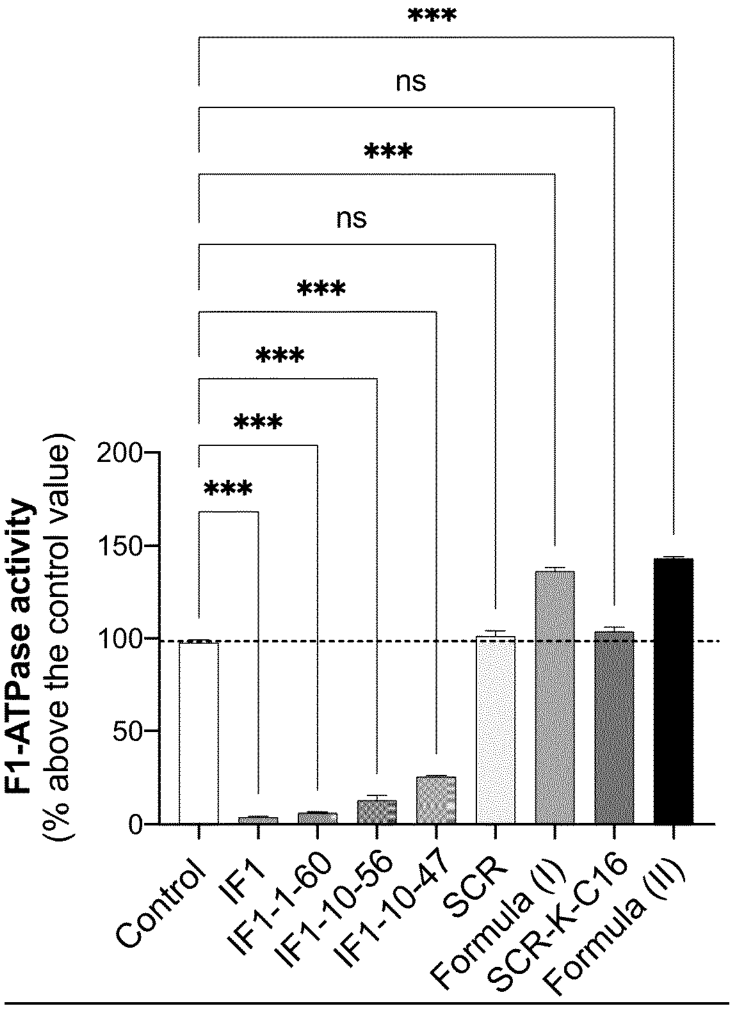
FIG. 3 represents the effect of human IF1, peptides derived from mature human IF1 (1-60, 10-56, 10-47), peptide of formula (I) and peptide of formula (II) on the ATPase activity of human F1Fo-ATPase (F1-ATPase activity). F1-ATPase activity assay was measured as described in Materials and Methods in the presence of IF1 (1 μM), IF1-derived peptides (1 μM each), peptide of formula (I) (1 μM), peptide of formula (II) (1 μM) or scramble peptides (SCR and SCR-K-C16, 1 μM each). The results expressed as a percentage of control (PBS). n=3 independent experiment per condition. Data are expressed as mean±SEM and analyzed by one-way ANOVA followed by Dunnett's multiple comparisons test versus control unless otherwise mentioned. ***$p<0.001$, ns: non statistically significant.

The results are presented in FIG. 3. Human IF1, IF1-1-60, IF1-10-56 and IF1-10-47 (1 μM each) strongly inhibited the F1-ATPase activity. As expected IF1 displays the strongest inhibitory activity (96% inhibition as compared to control), followed by IF1-10-60 (94%) then IF1-10-56 (88%) and IF1-10-47 (75%). Conversely, the peptide of formula (I) and the peptide of formula (II) stimulated F1-ATPase activity by 36 and 43% respectively while their respective scramble peptide, SCR and SCR-K16, had no effect.

Conclusion

Unlike IF1 and other peptides derived from the IF1 sequence, the peptide of formula (I) and the peptide of formula (II) do not inhibit but stimulate the F1-ATPase activity. These peptides are therefore F1-ATPase activator.

Example 4: In Vitro Activity of the Peptide of Formula (I) and the Peptide of Formula (II): F1-ATPase Activation Materials and Methods The human hepatocyte cell line HepG2 was obtained from the American Type Culture Collection (#HB-8065). HepG2 were cultured in Dulbecco's Modified Eagle's Medium (DMEM)—high glucose (D0822, Sigma-Aldrich) supplemented with 10% fetal bovine serum (10270098, Life technologies), 1% Penicillin-Streptomycin solution (P0781, Sigma-Aldrich). HepG2 cells were seeded on 24-well plates at 75,000 cells/well (Day 0). After 24 hours of growing, cells were serum starved for 24 h in order to synchronize cell cycles (Day 1) and then replaced additional 24 h in complete cell growth medium (Day 2). On day 3, cells were washed and equilibrated in fresh DMEM—high glucose without red phenol for 1 h (D1145, Sigma-Aldrich).

The cells were then treated 5 min with different concentration of peptide of formula (I) (0.1 to 5 μM), the peptide of formula (II) (1 μM), SCR (1 μM), SCR-K-16 (1 μM) or apoA-I (10 μg/mL) purified from human plasma [5].

Specific ecto-F1-ATPase activation was assessed in the presence of IF1 protein (1 μM), a natural inhibitor of $F_1$-ATPase that interacts with the β-subunit to inhibit the ATP hydrolysis activity [1] [5].

Supernatants were then collected and centrifuged (10,000 g, 5 min, 4° C.) and processed for ADP and ATP measurement. For ADP measurement, ADP was converted into ATP in 150 mM NaCl, 5 mM KCl, 2 mM MgCl2, pH 7.5 buffer containing 0.5 mM phosphoenolpyruvate (PEP) and pyruvate kinase (PK, 6 U per point for 15 min at 37° C.). For ATP measurement, 100 μl of sample was analyzed using the ATP bioluminescence assay kit CLS II (Roche Diagnostics). Samples were added to the ATP assay mixture and luminescence was measured in a microplate reader Infinite F500 (Tecan, Switzerland) for 1000 ms. The ATP standard curve was produced in the same medium as the samples and in the $10^{-5}$ to $10^{-10}$ M concentration range. The ADP concentration was then calculated as the ATP concentration following ADP conversion minus the basal ATP concentration. Data are expressed as nanomoles of ADP produced.

Results

Figure 4:
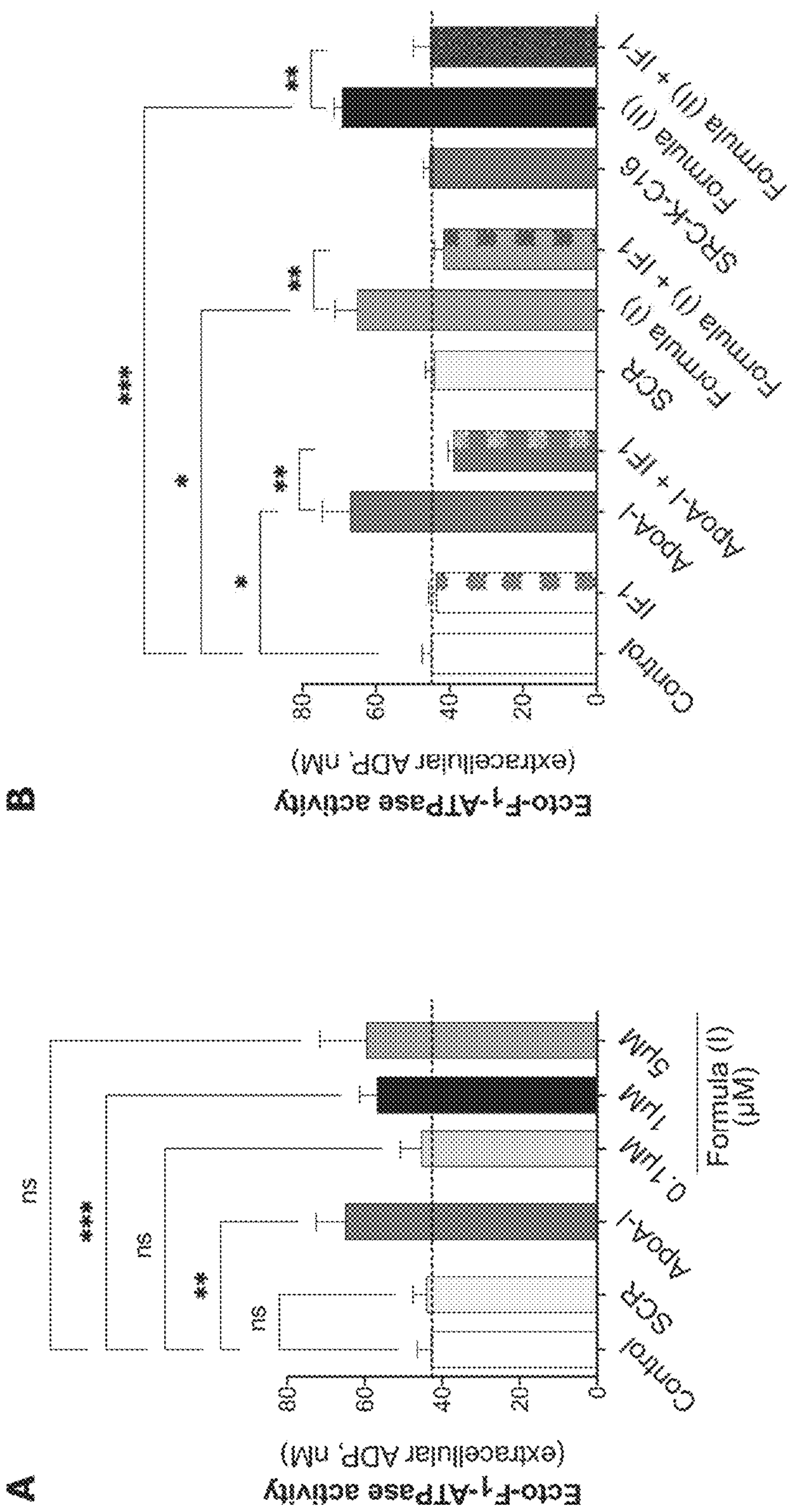
FIG. 4 represents the effect of the peptide of formula (I) and the peptide formula (II) on ecto-F1-ATPase activity, analyzed by the measurement of extracellular ADP content. Extracellular ADP concentration was measured by luciferin-luciferase assay as described in Materials and Methods. The contribution of ecto-F1-ATPase activity to extracellular ADP concentration was assessed by using the F1-ATPase inhibitor, IF1. (A) HepG2 cells were incubated for 5 min with increasing concentration of the peptide of formula (I) and extracellular ADP concentration was measured. Scramble peptide (SCR, 1 μM) and apoA-I (10 μg/mL) were used as negative and positive controls, respectively (n=3-7 per condition). (B) HepG2 cells were pre-incubated for 10 min with or without IF1 (1 μM) then treated with apoA-I (10 μg/mL, positive control), peptide of formula (I) (1 μM), peptide of formula (II) (1 μM) or scramble peptides (SCR and SCR-K-C16, 1 μM) for 5 min and extracellular ADP concentration was measured. n=3-7 independent experiment per condition. Data are expressed as mean±SEM and analyzed by one-way ANOVA followed by Dunnett's multiple comparisons test versus control (PBS) unless otherwise mentioned. *$p<0.05$, $p<0.01$, *$p<0.001$, ns: non statistically significant.

The results are presented in FIG. 4. Under physiological conditions, ecto-F1Fo-ATPase worked catalytically in a direction opposite to that described in functional mitochondrial. Indeed apoA-I binding to ecto-F1Fo-ATPase stimulated the hydrolysis of extracellular ATP into ADP, and phosphate and this process is inhibited by IF1, a natural inhibitor of F1-ATPase [1]. Here we used IF1 to inhibit ecto-F1-ATPase activity [5]. As expected, incubation of HepG2 cell with apoA-I increased extracellular ADP concentration (FIG. 4A), and inhibition of F1-ATPase activity with IF1 blunted this effect (FIG. 4B), which reflects the ability of apoA-I to stimulate ecto-F1-ATPase hydrolytic activity. The peptide of formula (I) increased extracellular ADP concentration in a dose-dependent manner with a maximum efficacy reached at 1 μM (FIG. 4A), and inhibition with IF1 blunted this effect (FIG. 4B). Similar results were observed with 1 μM of the peptide of formula (I) (FIG. 4B). Those results indicate that both peptides of formula (I) and peptide of formula (II) stimulated ecto-F1-ATPase hydrolytic activity.

Conclusion

The peptide of formula (I) and the peptide of formula (II) stimulated ecto-F1-ATPase activity in hepatocytes, and competed with the binding of IF1 to cell surface F1Fo-ATPase. These peptides are therefore good candidates for activating cell surface F1Fo-ATPase.

Example 5: In Vitro Activity: HDL Endocytosis by Hepatocytes

Materials and Methods

HDL Endocytosis Assays.

HepG2 cells were seeded on 96-well plates at 50,000 cells/well. $HDL_3$ (d 1.12-1.21) were isolated from plasma of healthy human donors [12] and referred to as HDL. HDL was fluorescently labeled with AlexaFluor®568 dye (A10238, Thermofisher Scientific) according the instructions of manufacturer. 1 h30 before the assay, the cells were serum starved for 1 h30 in order to stabilize nucleotide secretion. Cells were incubated with inhibitors (H49K, 1 μM) for 10 min before treatment with the different peptides (1 μM) or apoA-I (10 μg/ml) purified from human plasma [5]. 5 min after peptide treatment, endocytosis was initiated by 50 μg/mL of AlexaFluor568®-labelled HDL. The same experiment was performed with a 25-fold excess of unlabelled HDL (2.5 mg/mL) to determine the nonspecific fluorescence signal. After 25 min at 37° C., cells were then washed in serum-free DMEM and extracellular membrane-bound HDL was disassociated by incubating cells at 4° C. in serum-free DMEM for 90 min. Following washes, cells were lysate in NaOH 0.1M SDS 1% during 2 h, lysates were transferred in a black 96-wells plate and fluorescence was recorded at 568 nm (Varioscan flash). Fluorescence for each condition was substrate with the value obtained in unlabelled HDL condition, and results were expressed as the fold change as compared with the basal condition (untreated cells).

Results

Figure 5:
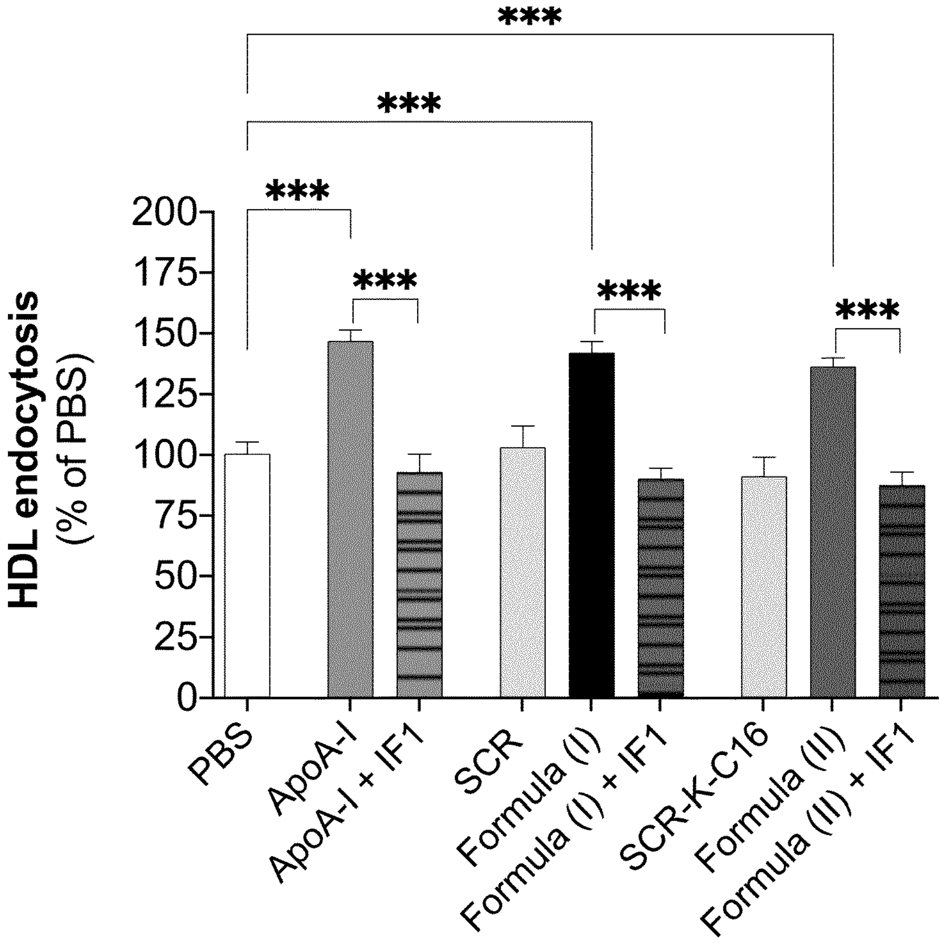
FIG. 5 represents the effect of the peptide of formula (I) and the peptide of formula (II) on HDL endocytosis by human hepatocytes. HepG2 cells were pre-incubated with apoA-I (10 μg/mL), the peptide of formula (I) (1 μM), the peptide of formula (II) (1 μM) or scramble peptides (SCR and SCR-K-C16, 1 μM), with or without IF1 (1 μM) then incubated for 25 min with HDL-Alexa568 (50 μg/mL) and cellular fluorescence content was quantified as described in Material and Methods. n=3-7 independent experiments per group. Data are expressed as the percentage (i SEM) above or below the control value (PBS) analyzed by one-way ANOVA followed by Dunnett's multiple comparisons test versus control (PBS) unless mentioned. ***$p<0.001$.

The results are presented in FIG. 5. F1Fo-ATPase-mediated HDL endocytosis pathway depends on the activation of cell surface F1Fo-ATPase by apoA-I and extracellular ADP production and P2Y receptor activation [6]. As previously reported in [7], apoA-I (10 μg/mL) has significantly stimulated HDL endocytosis by about 45% compared to non-stimulated cells in a process that strictly depends on ecto-F1-ATPase activity since pre-incubation with IF1 has abolished the effect of apoA-I on HDL endocytosis (FIG. 5). Similarly, the peptide of formula (I) (1 μM) and the peptide of formula (II) (1 μM) have stimulated HDL endocytosis and pre-treatment with IF1 (1 μM) has completely abolished this effect. SCR (1 μM) and SCR-K-C16 (1 μM) had no effect on HDL endocytosis which remained to the level of PBS treatment.

Conclusion

F1Fo-ATPase-mediated HDL endocytosis in hepatocytes was significantly increased when F1-ATPase activity is pharmacologically stimulated by the peptide of formula (I) and the peptide of formula (II). Given that HDL endocytosis in hepatocytes is one key last step of reverse cholesterol transport for excess cholesterol removal [6], the peptides of formula (I) and formula (II) are therefore good candidates to improve reverse cholesterol transport and excess cholesterol elimination from the body.

Example 6: In Vitro Activity: Endothelial Nitric Oxide (NO) Production

Materials and Methods

Nitric Oxide Production.

Nitric oxide (NO) was detected using a DAF-FM-DA probe (D2321, Sigma-Aldrich) which forms fluorescent benzotriazole when it reacts with NO. HUVEC cells (PromoCell #C-12203) were seeded in 96-well plates (10,000 cells per well) and cultured in endothelial cell basal medium 2 (PromoCell #C-22211) supplemented with GM2 supplement Mix (PromoCell #C-39211), until 80-90% confluence. The medium was then replaced with M-199 without serum for 4 h, and the cells were incubated for 45 min with DAF-FM-DA (5 μM) diluted in PBS. Cells were treated with increasing concentrations of the different peptides or apoA-I (10 μM) purified from human plasma [5] or histamine (1 mM) as positive control. In another set of experiments, cells were incubated with inhibitors (IF1, 1 μM) for 10 min before treatment with peptides or apoA-I. The fluorescence was recorded for 30 min (λex=495 nm, λem=515 nm) with a Tecan Flash Multimode Reader (Thermo Fisher Scientific). Fluorescence for each condition was compared with the value obtained in untreated cells, and results were expressed as the fold change as compared with the basal condition (untreated cells).

Results

Figure 6:
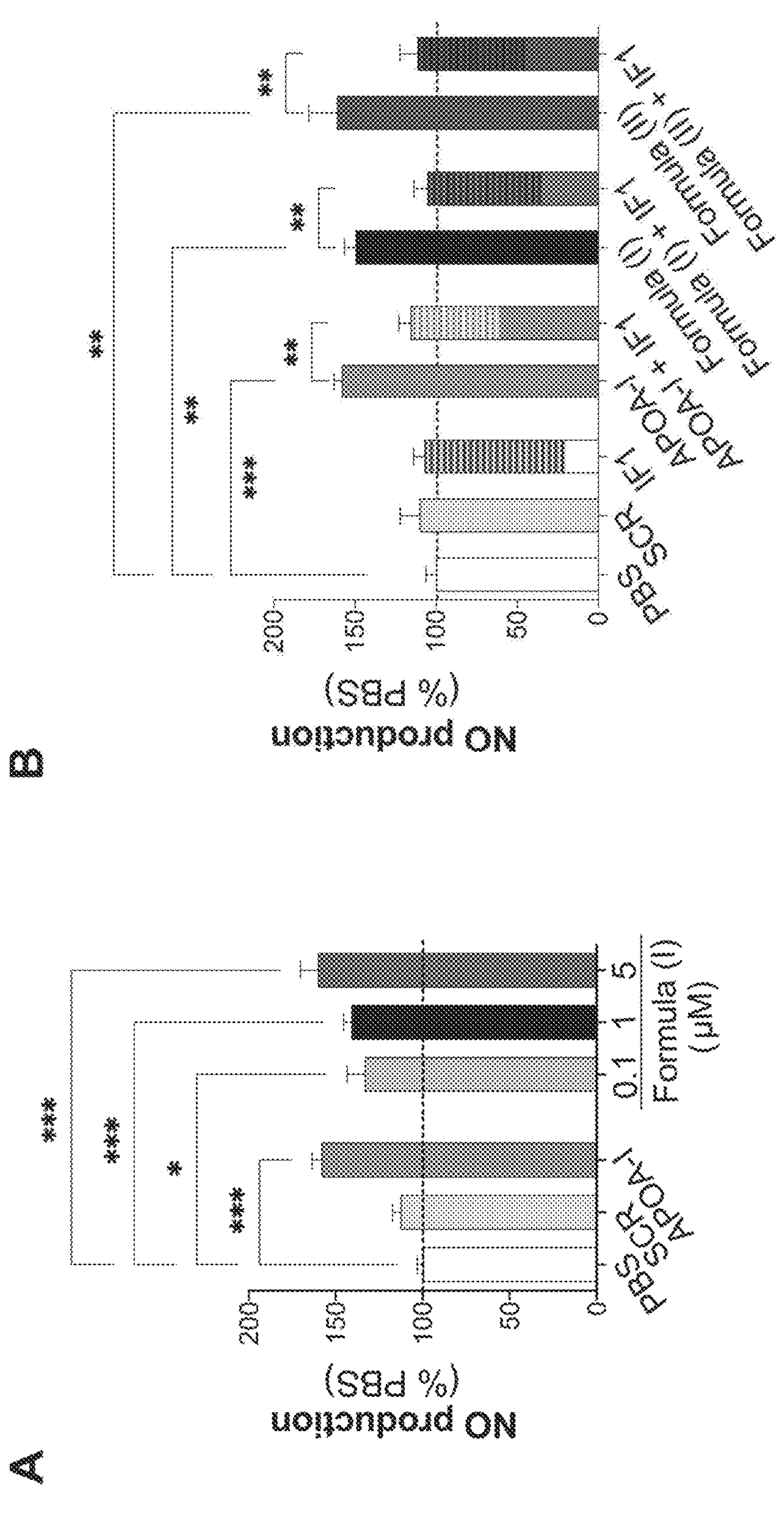
FIG. 6 represents the effect of the peptide of formula (I) and the peptide of formula (II) on nitric oxide (NO) production in human endothelial cells. NO production in HUVECs was measured by using the NO-sensitive fluorescence probe DAF-FM-DA as described in Material and Methods. Scramble peptide (SCR, 1 μM) and apoA-I (10 μg/mL) were used as negative and positive controls, respectively. (A) NO production under basal condition (PBS) or in the presence of increasing concentrations of the peptide of formula (I) for 10 min. n=3-6 independent experiments per group. (B) NO production under basal condition (PBS) or in the presence of the peptide of formula (I) (1 μM) or the peptide of formula (II) (1 μM) for 10 min with or without prior treatment for 10 min with IF1 (1 μM). n=3-6 independent experiments per group. Data are expressed as the percentage (i SEM) above or below the control value (PBS) analyzed by one-way ANOVA followed by Sudak's (A) or D Dunnett's (B) multiple comparisons test versus control (PBS) unless otherwise mentioned. *$p<0.05$, $p<0.01$, *$p<0.001$.

The results are shown in FIG. 6. Ecto-F1Fo-ATPase is expressed at the plasma membrane of endothelial cells and involved in NO production [5]. As described in [5], activation of ecto-F1Fo-ATPase by apoA-I stimulated NO production by endothelial cells (FIG. 6A) and this effect was abolished when cell are pre-treated with IF1 (FIG. 6B). Similarly, the peptide of formula (I) (1 μM) and the peptide of formula (II) (1 μM) stimulated by about 50% the production of NO production by endothelial cells and this effect was completely abolished by IF1 (FIG. 6B).

According to the protocol disclosed in [5], the peptide of formula (I) increased femoral artery blood flow in conscious wild-type C57B/L6J mice in a process that strictly depend on endothelial NO production (data not shown).

Conclusion

In human endothelial cells, F1Fo-ATPase-mediated NO production by eNOS was significantly increased when F1-ATPase activity is pharmacologically stimulated by the peptide of formula (I) and the peptide of formula (II). Given that NO production by eNOS preserves vascular homeostasis [16] and maintains quiescent both hepatic stellate cells, involved in liver fibrosis, and Kupffer cells, involved in liver inflammation [8], the peptides of formula (I) and formula (II) are therefore good candidates for the treatment of metabolic syndrome, cardiovascular disease (CVD), non-alcoholic fatty liver disease (NAFLD) or cholestatic liver disease.

Example 7: In Vitro Activity: Hepatic Steatosis

Materials and Methods

Preparation of Oleate and Palmitate Solution.

A solution containing 250 mM palmitate (P0500, Sigma-Aldrich) was first prepared in 0.1 M NaOH at 70 C for 30 min then diluted in DMEM low glucose (D5546, Sigma-Aldrich) containing 10% fatty acid-free BSA (A7030, Sigma-Aldrich) to yield a 10 mM palmitate solution and allowed to dissolve for 30 min at 37° C., filter sterilized and stored in glass vial at −20 C until use. This palmitate stock solution and ready to use oleate solution (03008, Sigma-Aldrich) were used to prepared a 0.5 mM solution at a 2:1 ratio of oleate to palmitate in complete culture medium containing DMEM low glucose, 10% fetal bovine serum, 1% Penicillin-Streptomycin and 1% fatty acid-free BSA.

In-Vitro Evaluation of Steatosis.

HepG2 cell were grown in 12-well plates to 60-70% confluence then exposed for 48 h to culture medium (DMEM low glucose, 10% fetal bovine serum, 1% Penicillin-Streptomycin and 1% fatty acid-free BSA) alone or containing 0.5 mM oleate/palmitate mixture (2:1) to induce steatosis. For the last 24 h of the 48 h period, cells were treated with 1 μM of the peptide of formula (I) or the peptide of formula (II).

Primary mouse hepatocytes were isolated as described in Example 3 from mice fed western-diet for 11-weeks (Envigo #TD.88137 containing 0.2% cholesterol, 42% kcal from fat, 34% sucrose by weight). Primary mouse hepatocytes were seeded in a 12-well plate at a density of 600,000 cells/well in growth medium and treated for 24 h with apoA-I (10 μg/mL), peptide of formula (I) (1 μM) or peptide of formula (II) (1 μM).

For measurement of intracellular triglyceride content, cells were washed with PBS and scraped in 5% NP-40 lysis buffer and heated for 10 min at 85° C. Triglycerides were then quantified using triglyceride commercial kit (Biolabo #87319). Values were normalized to protein concentration in cell lysates.

Results

Figure 7:
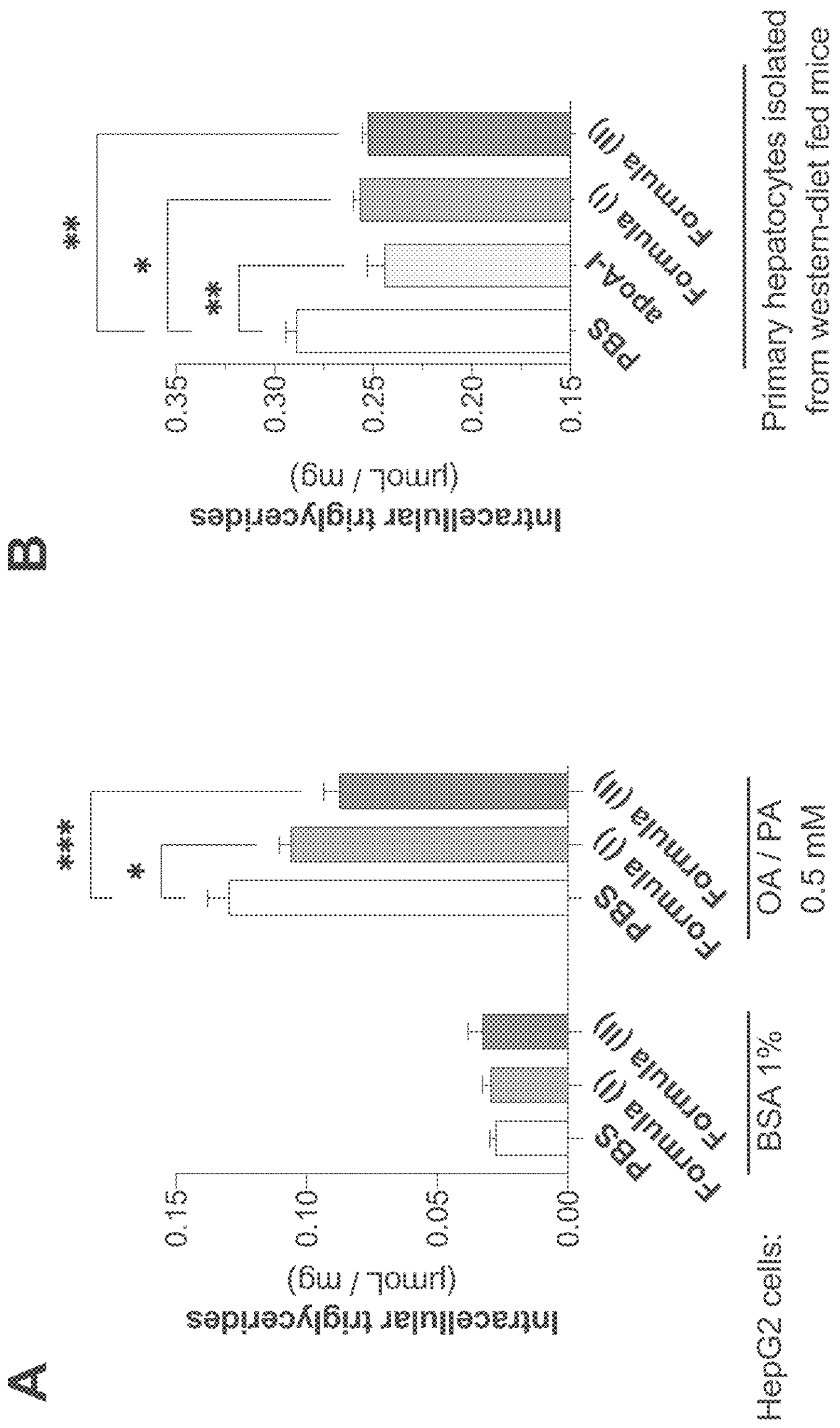
FIG. 7 represents the effect of peptide of formula (I) and the peptide of formula (II) on oleate/palmitate-induced steatosis in human hepatocytes (HepG2 cells) and primary mouse hepatocytes. (A) HepG2 cells were cultured for 48 h in medium containing 1% BSA (vehicle) or oleic acid (OA, 0.33 mM) and palmitic acid (PA, 0.16 mM) (OA:PA, 2:1) to induced steatosis. Following the induction of steatosis for 24 h, cells were incubated for 24 h with the peptide of formula (I) (1 μM) or the peptide of formula (II) (1 μM). Cells were then scraped in 5% NP-40 buffer for quantification of intracellular triglycerides content. (B) Primary mouse hepatocytes isolated from C57BL/6J mice fed western-diet were incubated for 24 h with apoA-I (10 μg/mL), peptide of formula (I) (1 μM) or the peptide of formula (II) (1 μM). n=7 independent experiments per group. Data are expressed as mean (i SEM) analyzed by one way ANOVA Dunnett's multiple comparisons test versus control (PBS). *$p<0.05$, $p<0.005$, *$p<0.001$.

The results are presented in FIG. 7. HepG2 cells exposed to fatty acids (0.5 mM solution at a 2:1 ratio of oleate to palmitate) showed more than 300% higher intracellular triglyceride content compared to untreated cells (vehicle, BSA 1%) (FIG. 8A). Compared to the PBS control, this intracellular accumulation of triglycerides induced by fatty acids was significantly reduced by 18% when HepG2 cells are treated with the peptide of formula (I) ($p<0.05$, FIG. 7A) and by 32% when cell are treated with the peptide of formula (II) ($p<0.001$, FIG. 7A). Also, treatment for 24 h with the peptide of formula (I) and the peptide for formula (II) significantly reduced intracellular accumulation of triglycerides in steatotic primary mouse hepatocytes as compared to the PBS control ($p<0.05$ and $p<0.005$, respectively, FIG. 7B). A similar effect was observed when primary mouse hepatocytes were treated with apoA-I ($p<0.005$ as compared to PBS, FIG. 7B).

Conclusion

The peptide of formula (I) and the peptide of formula (II) did reduce steatosis in a model of steatotic human hepatocytes and in steatotic primary mouse hepatocytes. Given that steatotic hepatocytes are key drivers of the pathogenic process in NAFLD/NASH [11], the peptide of formula (I) and the peptide of formula (II) are therefore good candidates to prevent and treat non-alcoholic fatty liver disease (NAFLD) and non-alcoholic steatohepatitis (NASH).

Example 8: In Vitro Toxicity Assay (Hepatocytes)

Materials and Methods

Cytotoxicity Assays.

HepG2 cells were seeded in a 96-well plate at a density of 10,000 cells/well in growth medium (DMEM high-glucose, 10% fetal bovine serum). The next day, growth medium was changed and the peptide of formula (I) was added once with ascending dose for 24 h, 48 or 72 h or for 48 h with repeating once in 24 h. Similarly, the peptide of formula (II) was added once with ascending dose for 24 h or 48 h or for 48 h with repeating once in 24 h. Cells were incubated for 4 h with 5 mg/L MTT and 100 μL of DMSO was added in the well. Absorbance was recorded at 570 and 660 nm using the microplate spectrophotometer system (Varioscan flash). Cell viability was calculated by subtracting the 570 nm absorbance to the background measured at 660 nm.

Results

Figure 8:
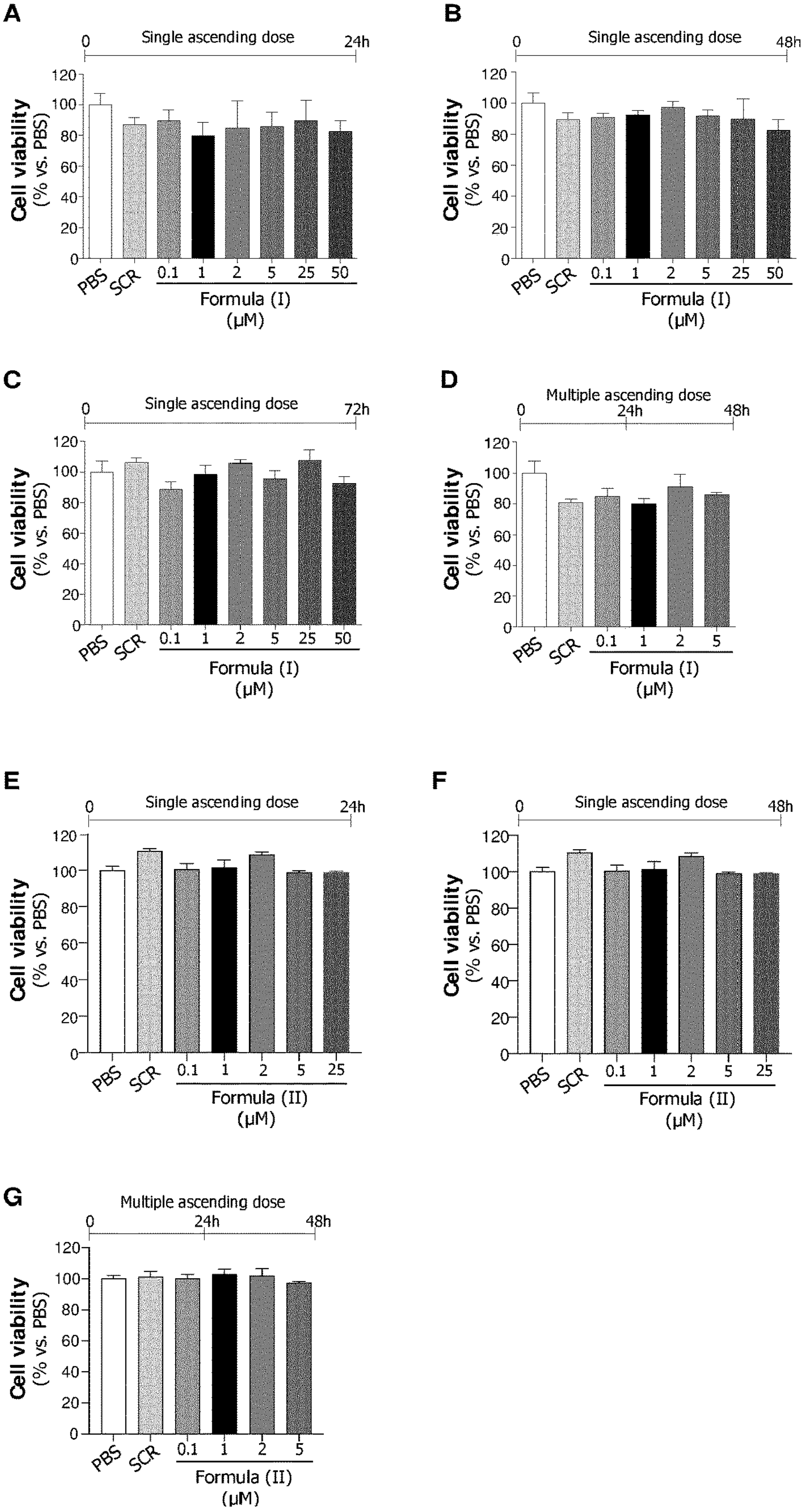
FIG. 8 represents the effect of the peptide of formula (I) and the peptide of formula (II) on cytotoxicity in human hepatocytes (HepG2 cells). MTT assay was used to test cell growth rate and toxicity in HepG2 cells. (A) Cells were treated once with PBS (vehicle), scramble peptide (SCR, 1 μM) or ascending concentration of a single dose of the peptide of formula (I) for 24 h (A), 48 h (B) or 72 h (C) then MTT assay was performed. (D) Cell were treated with scramble peptide (SCR, 1 μM) or ascending concentrations of the peptide of formula (I) for 48 h with repeating dose one in 24 h then MTT assay was performed. n=3 independent experiments per group. Data were expressed as the percentage (i SEM) above or below the control value (PBS) analyzed by Kruskal-Wallis test with Dunn's post hoc versus control (PBS). No significant differences were observed.

The results are shown in FIG. 8. Treatment of hepatocytes with single ascending dose of the peptide of formula (I), from 0.1 to 50 μM, for 24, 48 or 72 h had no impact on cell viability, neither at multiple ascending doses at 24 and 48 h. Treatment of hepatocytes with single ascending dose of the peptide of formula (II), from 0.1 to 25 μM, for 24 or 48 h had no impact on cell viability, neither at multiple ascending doses at 24 and 48 h.

Conclusion

The peptide of formula (I) and the peptide of formula (II) did not display any cellular toxicity over time, neither with ascending single or repeated doses.

Example 9: Stability of the Peptide of Formula (I) and the Peptide of Formula (II) in PBS, Plasma and Serum

Materials and Methods

Reagents.

UPLC/MS-grade acetonitrile and water, phosphate buffer saline (PBS) and formic acid were purchased from Biosolve (Valkenswaard, Netherlands).

Stability Assays.

Peptide of Formula (I) or peptide of Formula (II) were prepared at a concentration of 200 μg/mL in PBS or mixed with EDTA plasma or serum from human (Etablissement Frangais du Sang, EFS) or mouse (C57BL/6J, cardiac puncture). Aliquots from PBS samples (40 μL) were incubated at 4° C. or 37° C. for 0, 1, 2 and 4 weeks. Aliquots from plasma and serum samples (50 μL) were incubated at 4° C. or 37° C. for 0, 1, 2, 4, 6, 12, 24 h.

Sample Analysis.

A mixed solution of peptides of formula (I) and (II) was constituted and serially diluted in PBS to obtain seven standard solutions, ranging from 200 μg/mL to 0.2 μg/mL. In parallel, a mixed solution of labelled peptides of Formula (I) and (II) (Thermo Scientific, Biopolymers Darmstadt, Germany) was prepared in PBS at 100 μg/mL. The mixed solution of labelled peptides (25 μL) was added to 25 μL of standard solutions as well as to PBS, plasma and serum samples. Acetonitrile (150 μL) was added to each sample to precipitate plasma/serum proteins. After centrifugation (10,000×g, 4° C., 10 min), the clear supernatants (150 μL) were dried under a gentle stream of nitrogen (45° C.), reconstituted with 10% acetonitrile containing 0.1% formic acid (100 μL), and injected into the liquid chromatography-high-resolution mass spectrometry (LC-HRMS) system. LC-HRMS analyses were performed on an H-Class UPLC system (Waters Corporation, Milford, MA, USA) by injection of 10 μL of samples onto an Acquity® Peptide CSH $C_{18}$ column (2.1 mm×150 mm, 1.7 μm; Waters Corporation) held at 60° C. The mobile phase was composed of 5% acetonitrile as solvent A and 100% acetonitrile as solvent B, each containing 0.1% formic acid. The elution was carried out using a gradient of solvent B in solvent A over 20 min at a constant flow rate of 250 μL/min. Mobile phase B was kept constant at 1% for 1 min, linearly increased from 1% to 80% for 15 min, kept constant for 1 min, returned to the initial condition over 1 min, and kept constant again for 2 min before the next injection. HRMS detection was performed by a Synapt G2 HRMS Q-TOF mass spectrometer equipped with a Z-Spray interface for electrospray ionization (Waters Corporation). The resolution mode was applied in a mass-to-charge (m/z) ratio ranging from 200 to 4,000 at a mass resolution of 25,000 Full Width Half Maximum in the positive ionization mode. Ionization parameters were as follow: capillary voltage of 3 kV, cone voltage of 30 V, desolvatation gas flow of 900 L/hr, source temperature of 120° C., desolvatation temperature of 450° C., Nitrogen as desolvatation gas. Data were collected in the continuum mode at a rate of four spectra per second. Leucine enkephalin solution prepared at 2 μg/mL in an acetonitrile/water (50/50, v/v) mixture was infused at a constant flow (10 μL/min) in the lock spray channel. A spectrum of 1 s was acquired every 20 s and allowed mass correction during experiments. Peptides were analyzed according to their major exact m/z (i 5 ppm, Table 1) and each peptide signal was normalized with that of its labelled internal standard. Peptide concentrations were calculated using calibration curves plotted from standard solutions (linear regression, 1/x weighted, origin excluded).

TABLE 1

Mass spectrometry parameters used for peptide detection by LC-HRMS.

| Peptide | Sequence | Major m/z | Charge state |
|---|---|---|---|
| Formula (1) | Acetate-RGAGSIREAGGAFGKREQAEEERYFRAQSRE-amide | 590.9703 | 6+ |
| Formula (1) (IS) | Acetate-RGAGSI-[$^{13}C_6$, $^{15}N_4$]R-EAGGAFGKREQAEEERYF-[$^{13}C_6$, $^{15}N_4$]R-AQSRE-amide | 592.6370 | 6+ |
| Formula (II) | Acetate-RGAGSIREAGGAFGKREQAEEERYFRAQSREK-Palmitoyl | 652.1923 | 6+ |
| Formula (II) (IS) | Acetate-RGAGSI-[$^{13}C_6$, $^{15}N_4$]R-EAGGAFGKREQAEEERYF-[$^{13}C_6$, $^{15}n_4$]R-AQSREK-Palmitoyl | 653.8590 | 6+ |

IS: internal standard

Results

Figure 9:
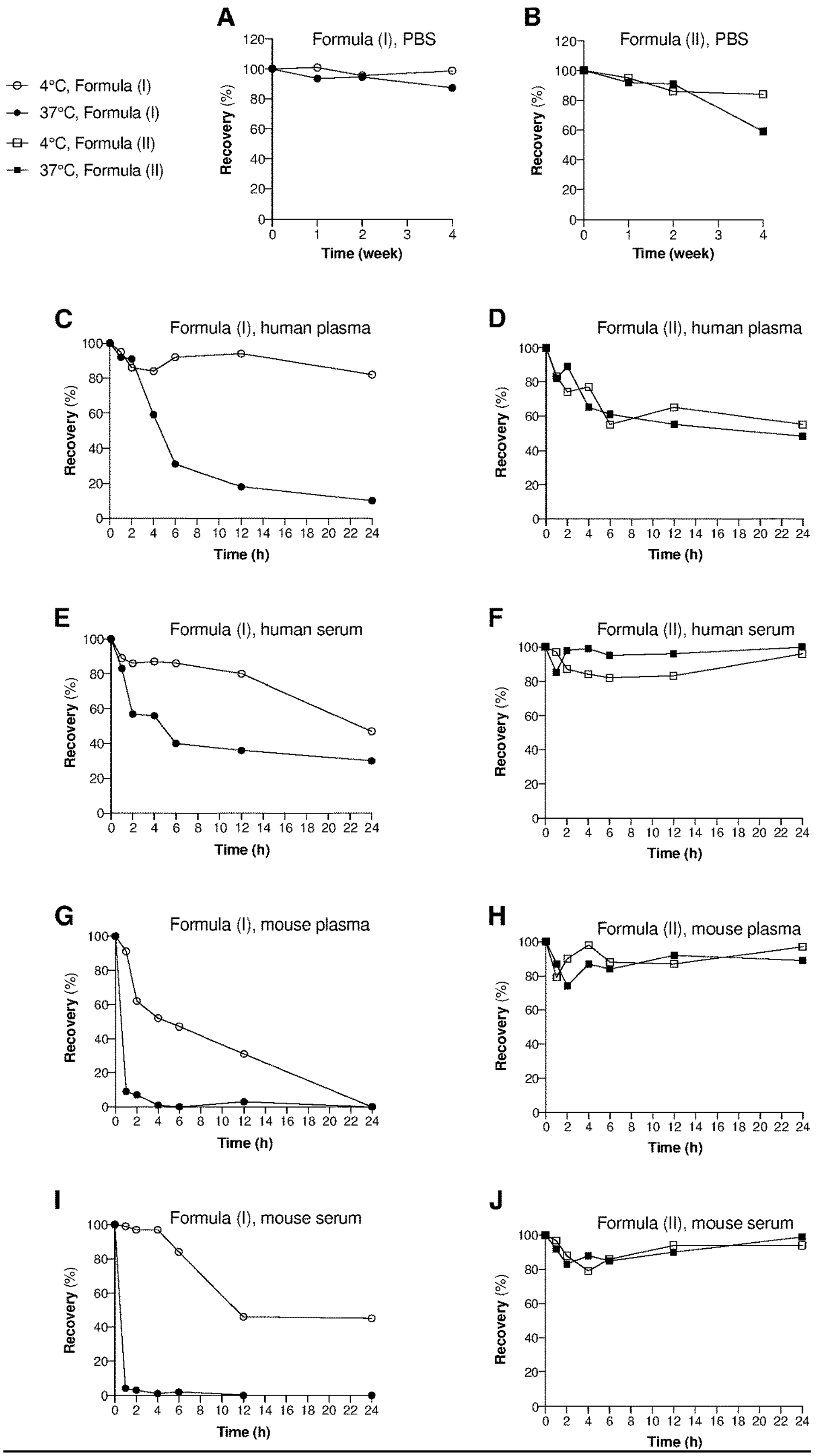
FIG. 9 represents the degradation over the time of the peptide of formula (I) (circle) and the peptide of formula (II) (square) at 4° C. (open shapes) and 37° C. (full shape) in PBS (A, B), human plasma (C, D), human serum (E,F), mouse plasma (G, H) and mouse serum (I, J). Peptide amounts were calculated relative to the quantities determined at time point zero.

The results are shown in FIG. 9 that represents peptide stability over time at 4° C. and 37° C. in different matrices (PBS, human and mouse serum, human and mouse plasma). The peptide of formula (I) and the peptide of formula (II) were stable at 4° C. and 37° C. in PBS for 4 weeks (FIG. 9A-B). The peptide of formula (I) and the peptide of formula (II) were both faster degraded in human plasma than in human serum (FIG. 9C-F). Same observation was observed for the peptide of formula (I) in mouse plasma and serum (FIGS. 9G and 9I) while the peptide of formula (II) was as stable in mouse serum as in mouse plasma (FIGS. 9H and 9J). When comparing peptide stability at 37° C. versus 4° C., the peptide of formula (I) was faster degraded at 37° C. than at 4° C. in any tested matrices (serum and plasma) and species (human and mouse), while no significant difference was observed in the stability of the peptide of formula (II) between 37° C. and 4° C. At 37° C., the peptide of formula (II) was much less degraded than the peptide formula (I) in both serum and plasma: at 37° C. for 24 h, the recovery of the peptide of formula (II) was 100% in serum and 50% plasma, versus only 30% and 10% for the peptide of formula (I).

Conclusion: The peptide of formula (I) and the peptide of formula (II) can be stored in PBS for at least 4 weeks at 4° C. and up to 37° C., without being degraded. The peptide of formula (II) presents little degradation in human and mouse biological matrices, including at 37° C. and up to 24 h, and is thus more suitable than the peptide of formula (I) for chronic injection.

Example 10: Pharmacokinetics of the Peptide of Formula (I) and the Peptide of Formula (II) In Vivo

Material and Method

LC-MS/MS Peptide Quantification.

The peptide of formula (I) and the peptide of formula (II) were analyzed in mouse EDTA plasma using a validated assay involving trypsin proteolysis and the subsequent analysis of a signature peptide (SEQ ID NO: 3) by liquid chromatography-tandem mass spectrometry (LC-MS/MS). The working solution of unlabeled peptide (SEQ ID NO: 3, 1 mM) was serially diluted in water to obtain 7 standard solutions ranging 0.05-5 μM. Plasma and standard samples (40 μL) were reduced, alkylated and trypsin-digested overnight using the ready-to-use solutions of the ProteinWorks™ eXpress kit (Waters Corporation, Milford, MA, USA), according to the manufacturer's instructions (except trypsin incubation time optimized to 7 h). The working solution of the labeled proteotypic peptide ([SEQ ID NO: 4]-[$^{13}C_6$, $^{15}N_4$]-K, 1 mM) was used as internal standard (IS) and added to the digestion buffer to a final concentration of 0.5 μM. After digestion, samples were cleaned using 30 mg Oasis HLB 1 cc Cartridges (Waters Corporation). Cartridges were conditioned, equilibrated, loaded, washed and eluted with methanol (1 mL), water (1 mL), samples (~200 μL), 5% methanol containing 0.1% TFA (1 mL) and 60% methanol containing 0.1% TFA (1 mL), respectively. Eluates were dried under a nitrogen stream, reconstituted with 100 μL of 10% acetonitrile containing 0.1% formic acid, and 10 μL were injected into the LC-MS/MS system. LC-MS/MS analyses were performed on a Xevo® TQD mass spectrometer with an electrospray (ESI) interface and an Acquity H-Class® UPLC™ device (Waters Corporation). Proteotypic peptides were separated over 9 min on an Acquity® BEH $C_{18}$ column (2.1×100 mm, 1.7 μm, Waters Corporation) held at 60° C. with a linear gradient of mobile phase B (100% acetonitrile) in mobile phase A (5% acetonitrile), each containing 0.1% formic acid, and at a flow rate of 600 μL/min. Mobile phase B was linearly increased from 1% to 50% for 5 min, kept constant for 1 min, returned to the initial condition over 1 min, and kept constant for 2 min before the next injection. Proteotypic peptides were then detected by the mass spectrometer with the ESI interface operating in the positive ion mode (capillary voltage, 3 kV; desolvatation gas ($N_2$) flow and temperature, 900 L/h and 400° C.; source temperature, 150° C.). The multiple reaction monitoring mode was applied for MS/MS detection (SEQ ID NO: 3, m/z 368.8→536.5, $y_6^+$; [SEQ ID NO: 4]-[$^{13}C_6$, $^{15}N_4$]-K, m/z 372.8→544.4, $y_6$) with cone and collision voltages set at 20 and 14 V, respectively. Data acquisition and analyses were performed with MassLynx® and TargetLynx® software, respectively (version 4.1, Waters Corporation). Chromatographic peak area ratio between unlabeled peptide and IS constituted the detector responses. Standard solutions were used to plot calibration curves for peptide quantification. The linearity was expressed by the mean $r^2$ which was greater than 0.998 (linear regression, 1/x weighting, origin excluded). Each sample was assayed three times and the coefficients of variation did not exceed 4.5%. The peptide of formula (I) and the peptide of formula (II) concentrations were expressed in μM assuming 1 mole of peptide equivalent to 1 mole of the peptide of formula (I) and the peptide of formula (II), respectively. Concentrations were then converted to their standard unit (ng/mL) assuming molecular weights of 3540 Da and 3917 Da for the peptide of formula (I) and the peptide of formula (II), respectively.

Animals.

Wild-type C57B/L6J male mice were purchased from Janvier Labs (Le Genest Saint Isle, France). Mice were caged in animal rooms under specific pathogen free conditions at the animal facility of Rangueil (Anexplo platform, US006, Toulouse, France) with a light/dark schedule of 12 h/12 h and were fed ad libitum with a normal chow diet (#V1535 R/M-H, Ssniff, Germany). All animal experimental procedures were conducted in accordance with institutional guidelines on animal experimentation approved by the local ethical committee of animal care and are conformed to the guidelines from Directive 2010/63/EU of the European Parliament on the protection of animals used for scientific purposes or the NIH guideline.

Pharmacokinetics (PK) Studies.

8-weeks old C57B/L6J male mice weighting 24.5±1.3 g were used for the following pharmacokinetic studies. All animals were allowed free access of food and water during the experiments. The peptide of formula (I) was administrated at 25 mg/kg, either intravenously (i. v.) at the tail vein or subcutaneously (s.c.). The peptide of formula (II) was subcutaneously administered 25 mg/kg. Three different animals were used for each time point. After administration, intracardiac blood was collected at 0.03, 0.117, 0.25, 0.5, 0.75, 1, 1.5, 2, 4 h for the peptide of formula (I) and 0.03, 1, 4, 6, 8, 10, 12, 16, 20, 24, 30, 48 h for the peptide of formula (II). EDTA was used as the anticoagulant and plasma was separated by centrifugation at 4,000 rpm for 10 min at 4° C. Plasma samples were placed on wet ice and, within 1 hour after collection, were stored at −80° C. until analyzed by liquid chromatography-mass spectrometry/mass spectrometry (LC-MS/MS) for quantification. Table 2 reports the calculated pharmacokinetics parameters in plasma, namely distribution and elimination half-lives ($t_{1/21bd1}$ and $t_{1/21bdz}$), maximum concentration ($C_{max}$), time to reach $C_{max}$ ($T_{max}$), Area Under the Curve (AUC), total plasma clearance (Cl), volume of distribution (Vd), mean residence time (MRT).

TABLE 2

Pharmacokinetics characteristics of the peptide of formula (I) and the peptide of formula (II)

| | iv-peptide of formula (I) | sc-peptide of formula (I) | sc-peptide of formula (II) |
|---|---|---|---|
| Dose, mg/kg | 25 | 25 | 25 |
| $t_{1/2}$lbd1, $^h$ | 0.06 (3.8 min) | 0.19 (11.6 min) | 2.09 (125.3 min) |
| $t_{1/2}$lbdz, $^h$ | 0.26 (15.8 min) | 0.22 (13.4 min) | 12.54 (752.4 min) |
| $C_{max}$, mg/L | n.a | 8.29 | 25.60 |
| $T_{max}$, h | n.a | 0.25 (15 min) | 4 (240 min) |
| AUC, mg · h/L | 13290 | 6136 | 211323 |
| Cl, L/h/kg | 1.9 | 1.9 | 0.05 |
| Vd, L/kg | 0.7 | 0.5 | 1 |
| MRT, h | 0.14 (8.4 min) | 0.55 (33 min) | 5.81 (348.6 min) |

Results

Figure 10:
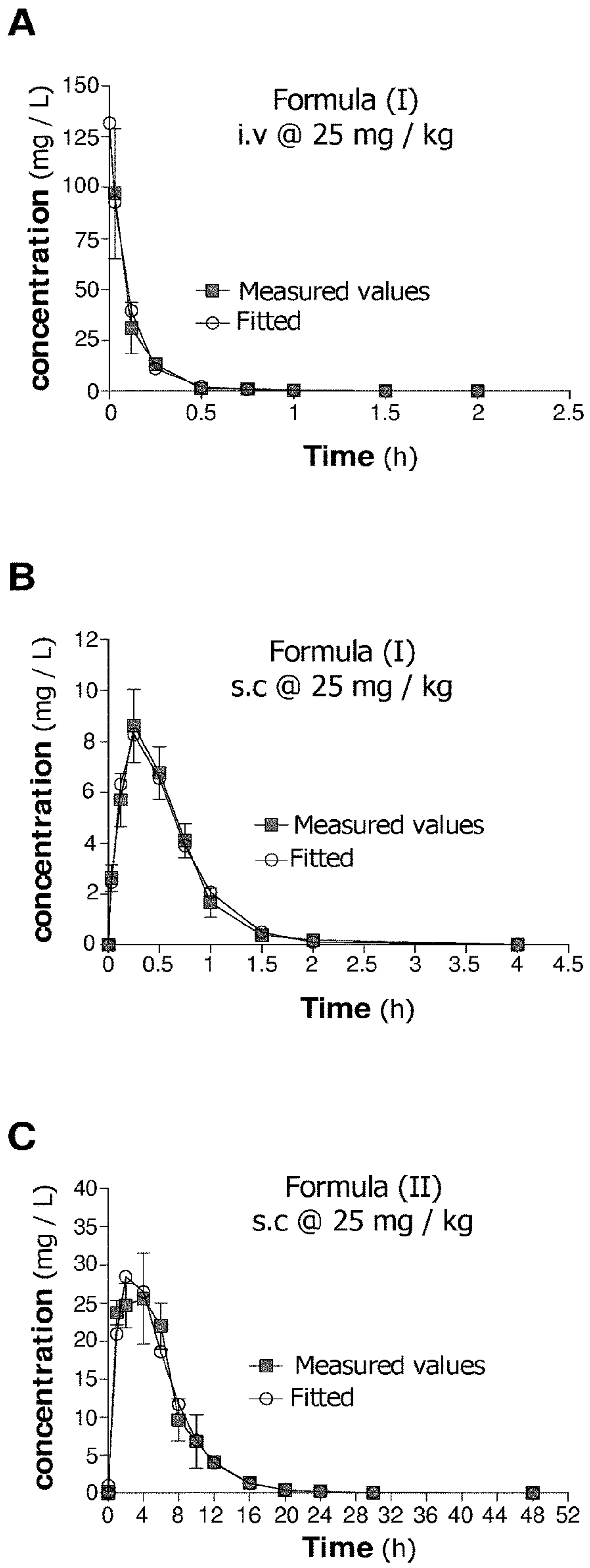
FIG. 10 represents the pharmacokinetic properties of the peptide of formula (I) and the peptide of formula (II) in mice. (A, B, C). The mean plasma concentration-time profile of the peptide of formula (I) (A-B) and the peptide of formula (II) (C) in mice plasma after intravenous (i. v., A) or subcutaneous (s.c., B-C) administration at 25 mg/kg (n=3 mice per time point for each condition). Filled square: mean concentration+/−SD; Open circle: generated data point from the fitted curve.

The results are presented in FIG. 10 and Table 2. Following intravenous (i. v.) and subcutaneous (s c.) administration of one dose at 25 mg/kg, the peptide of formula (I) was rapidly distributed and eliminated as illustrated in FIG. 10A (i.v.) and 10B (sc.). In these conditions, elimination half-life ($t_{1/21bdz}$) of the peptide of formula (I) was 0.26 h and 0.21 h for i. v. and s.c. administration, respectively (Table 2). The peptide of formula (I) displayed a moderate clearance (Cl=1.9 L/h/kg for both administration mode) and volume of distribution (Vd=0.7 L/kg and 0.5 L/kg for I.v. and s.c. administration, respectively).

In comparison to the peptide of formula (I), the peptide of formula (II) administrated subcutaneously at 25 mg/L was less rapidly distributed and eliminated (FIG. 10C), with an elimination half-life more than 50 time longer than for the peptide of formula (I) ($t_{1/21bdz}$=12.54 h), and a lower clearance (Cl=0.05 L/h/kg).

Conclusion

The peptide of formula (II) displayed improved pharmacokinetics properties as compared to the peptide of formula (I).

Example 11: In Vivo Efficacy of the Peptide of Formula (I) and the Peptide of Formula (II) on Biliary Lipid Secretions

Materials and Methods

Animals.

Wild-type C57B/L6J male mice were purchased from Janvier Labs (Le Genest Saint Isle, France). LDLR knockout mice (males, C57B/L6J background) were obtained from The Jackson Laboratory (Bar Harbor, Maine, USA). Mice were caged in animal rooms under specific pathogen free conditions at the animal facility of Rangueil (Anexplo platform, US006, Toulouse, France) with a light/dark schedule of 12 h/12 h and were fed ad libitum with a normal chow diet (#V1535 R/M-H, Ssniff, Germany). All animal experimental procedures were conducted in accordance with institutional guidelines on animal experimentation approved by the local ethical committee of animal care and are conformed to the guidelines from Directive 2010/63/EU of the European Parliament on the protection of animals used for scientific purposes or the NIH guideline.

Gallbladder Cannulation and Bile Collection.

Depending of experiments, 8 weeks old mice were intraperitoneally injected with PBS, the peptide of formula (I), the peptide of formula (II) and SCR. Details of peptide use, dose and mode of administration and time course are specified in the description of FIG. 11. Given the short elimination half-life of the peptide of formula (I), osmotic pumps were also used to insure a continuous delivery for 14 days. Briefly, 200 µL osmotic pump were filled with 10 mg/mL of the peptide of formula (I) in PBS and were implanted subcutaneously into the mice according to the manufacturer's instructions (Alzet®, model pump #2002), to insure the peptide of formula (I) release at an estimated rate of 0.5 µL/h, which corresponds to an estimated amount of delivery of 5 mg of the peptide of formula (I) per kilogram of body weight per day (5 mg/kg BW/day). Following treatments, mice were fasted for 2 h and were then anesthetized by intra-peritoneal injection of ketamine and xylazine hydrochloride. The common bile duct was ligated close to the duodenum and the gallbladder was punctured and cannulated with a polyethylene-10 catheter. After 30 min of stabilization, newly secreted bile was collected for 30 min. During bile collection, body temperature was stabilized using a temperature mattress. Bile flow (expressed in µL/min/100 g of body weight) was determined gravimetrically assuming a density of 1 g/mL for bile. At the end of experiment, blood was collected and mice were sacrificed by cervical dislocation.

Biliary Lipid Analyses.

For bile acid analysis, 1 µL of bile samples was diluted with 99 µL of milliQ water then incubated with the work reagent (6 mg NAD, 0.5 M hydrazine hydrate buffer, 0.05 M Na-pyrophosphate) for 4 min. The mix was then incubated with a start reagent (0.03 M Tris-EDTA; 0.3 U/mL 3-alpha-OH steroid dehydrogenase) and measured for 30 min, under excitation of 340/330 nm and emission of 440/420 nm. For phospholipid analysis, 1 µL of bile samples was diluted with 49 µL of milliQ water then incubated with the work reagent (100 mM MOPS, pH 8; 0.55 mM HVA; 20 mM CaCl; 11 U/mL Phospholipase-D; 1.66 U/mL Peroxidase; 0.1% Triton X-100) for 4 min. The mix was then incubated with a start reagent (1 M MOPS, pH 8, 50 U/mL Choline oxidase) and measured for 67.5 min, under excitation of 340/330 and emission of 440/40. For cholesterol analysis, 1 µL of bile samples was diluted with 29 µL of milliQ water then was incubated with the work reagent (100 mM MOPS, pH 8, 0.25 mM HVA; 0.1% Triton X-100) for 4 min. The mix was then incubated with a start reagent (0.1 M MOPS, pH 8, 0.06 U/mL cholesterol oxidase, 0.15 U/mL cholesterol esterase, 0.45 U/mL Peroxidase, 0.06 mM Taurocholate) and measured for 45 min, under excitation of 340/330 nm and emission of 440/420 nm. Secretion values of bile acids, phospholipids and cholesterol were calculated by multiplying concentration and bile flow values, and expressed as nmol/min/100 g body weight (BW).

Results

Figure 11:
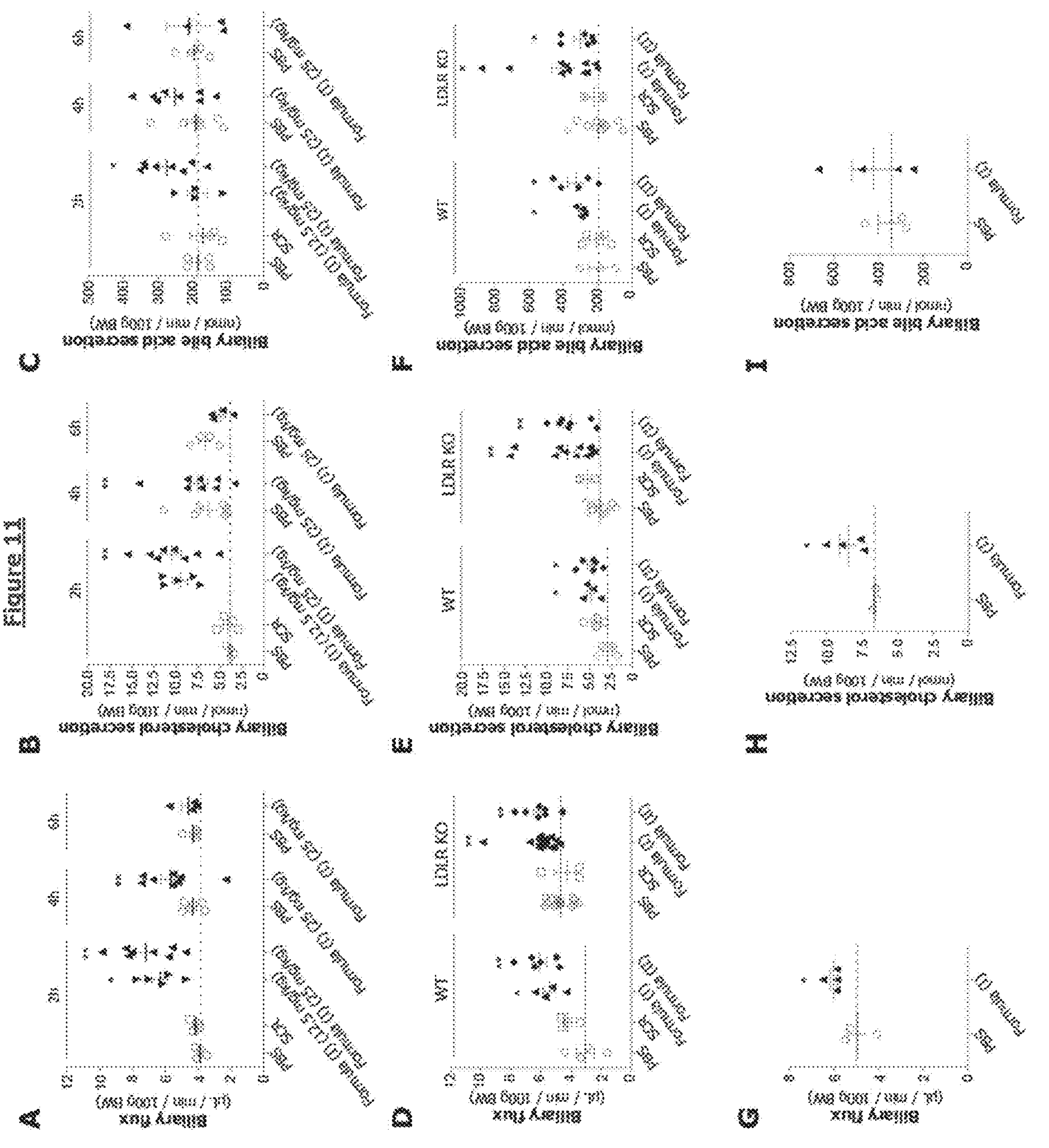
FIG. 11 represents the in-vivo efficacy of the peptide of formula (I) and the peptide of formula (II) on biliary lipid secretions in wild-type C57B/L6J and dyslipidemic LDLR KO mice. Bile flow (A), biliary cholesterol (B) and bile acids (C) secretions were measured in C57B/L6J mice at 2, 4, and 6 h following single dose of intraperitoneal (ip) administration of the peptide of formula (I) (12.5 mg/kg or 25 mg/kg), scramble peptide (SCR, 25 mg/kg) or vehicle (PBS). n=5-8 mice per group. Bile flow (D), biliary cholesterol (E) and bile acids (F) secretions were measured in C57B/L6J and LDLR KO mice at 2 h following single dose of intraperitoneal (ip) administration of the peptide of formula (I) (25 mg/kg), the peptide of formula (II) (25 mg/kg), SCR (25 mg/kg) or vehicle (PBS). n=4-6 per C57BL/6 mice group, n=7-15 per LDLR KO mice group. Bile flow (G) and biliary cholesterol (H) and bile acids (I) secretions were measured in C57BL/6J mice at 14 days following alzet osmotic pump subcutaneously placement to insure the peptide of formula (I) release at an estimated rate of 0.5 μL/h, which corresponds to an estimated amount of delivery of 5 mg of the peptide of formula (I) per kilogram of body weight per day (5 mg/kg BW/day). n=3-4 mice per group. Data are expressed as mean (i SEM) and are analyzed by Mann Whitney test versus control (PBS). *p<0.05, **p<0.01.

The results are presented in FIG. 11. C57BL/6 mice treated with an intraperitoneal bolus injection of 25 mg/kg the peptide of formula (I) displayed a significant increase of bile flux and biliary secretion of cholesterol and bile acids as compared to mice injected with PBS or 25 mg/kg SCR. This effect of the peptide of formula (I) was maintained up to 4 h following injection (FIG. 11A-C). As comparison, bolus injection of the peptide of formula (I) at 12 mg/kg was less efficient on biliary flux and biliary lipid secretion than the 25 mg/kg dose (FIG. 11A-C). Intraperitoneal bolus injection of 25 mg/kg the peptide of formula (II) in C57BL/6 mice also stimulated bile flux and biliary secretion of cholesterol and bile acids, to the same extent than similar treatment with the peptide of formula (I) (FIG. 11D-F). Those effects of the peptide of formula (I) and the peptide of formula (II) on stimulating biliary flux and biliary lipid secretion were also maintained in dyslipidemic LDL KO mice (FIG. 11D-F). The peptide of formula (I) also stimulated biliary flux and biliary cholesterol secretion when it was continuously delivered for 14 days at 5 mg/kg BW/day (FIG. 11G-I).

Conclusion

The peptide of formula (I) and the peptide of formula (II) stimulated biliary flux and biliary secretion of cholesterol and bile acids in both wild-type and dyslipidemic mice. Hepatic excretion of cholesterol in bile, either as bile acids or cholesterol, represent the main pathway of removing excess cholesterol responsible for atherosclerosis development [6]. Also, downregulation of biliary flux and biliary lipid secretion contributes to hepatic lipotoxicity and has been documented in NASH [13] and cholestatic liver condition [17]. Thus, the peptides of formula (I) and formula (II) are good candidates to protect against the development of metabolic syndrome, cardiovascular disease (CVD), non-alcoholic fatty liver disease (NAFLD) or cholestatic liver disease.

Example 12: In Vivo Efficacy of the Peptide of Formula (II) on the Development of NASH Associated Hepatic Steatosis Materials and Methods Animals.

Wild-type C57B/L6J male mice were purchased from Janvier Labs (Le Genest Saint Isle, France). Mice were caged in animal rooms under specific pathogen free conditions at the animal facility of Rangueil (Anexplo platform, US006, Toulouse, France) with a light/dark schedule of 12 h/12 h. At the initiation of the dietary intervention, all animals were 8 weeks old and were fed ad libitum with a normal chow diet (#V1535 R/M-H, Ssniff, Germany). All animal experimental procedures were conducted in accordance with institutional guidelines on animal experimentation approved by the local ethical committee of animal care and are conformed to the guidelines from Directive 2010/63/EU of the European Parliament on the protection of animals used for scientific purposes or the NIH guideline.

Mouse Model of Diet-Induced Hepatic Steatosis.

8 weeks old mice were fed fed western-diet for 4-weeks (Envigo #TD.88137 containing 0.2% cholesterol, 42% kcal from fat, 34% sucrose by weight). For the 2 last weeks of the 4-week period, mice were daily intraperitoneally administrated at 1 mg/kg/day with the peptide of formula (I) or PBS (control group). Following the treatment period, mice were fasted overnight, anesthetized by intra-peritoneal injection of ketamine and xylazine hydrochloride then killed by exsanguination. Body weight, liver triglyceride content, plasma lipids and transaminases were determined at sacrifice.

Liver Triglyceride Content.

100 mg of liver tissue were homogenized in 900 μL of phosphate buffer pH 7.4 until complete tissue lysis. Lipids were extracted by mixing 125 μL of lysates with 1 mL of $CHCl_3$:MeOH (2:1). After centrifugation, the chloroform phase was evaporated under nitrogen flux, and the dried residue was solubilized in 200 μL of isopropanol. Triglycerides were measured using commercial kits based on GPO-PAP detection method (Biolabo SA, Maizy, France). Results were expressed as mg of triglycerides/g liver.

Analyses of Plasma Lipid and Transaminase Levels

Triglycerides and cholesterol levels were determined using commercial colorimetric kits (Biolabo SA, Maizy, France) based on CHOD-PAP and GPO-PAP detection methods, coupling enzymatic reaction and spectrophotometric detection of reaction end products. Alanine-aminotransferase (ALT) and aspartate-aminotransferase (AST) levels were determined using a COBAS-MIRA+ biochemical analyser (Anexplo facility, Toulouse, France).

Oral Glucose Tolerance Test (OGTT)

After 8 weeks of diet, mice were treated after an overnight fasting period with an oral gavage glucose load (3 mg/g body weight). Blood glucose levels were measured by tail vein sampling with portable glucometer (Accu-check, Roche) 30 min before oral glucose load and at 0, 15, 30, 45, 60, 90 and 120 min after oral glucose load. Plasma insulin concentration was determined 30 min before and 15 min after glucose loading in 5 μL of plasma using an ELISA kit (Mercodia, Uppsala, Sweden) according to the manufacturer's instructions.

Results

Figure 12:
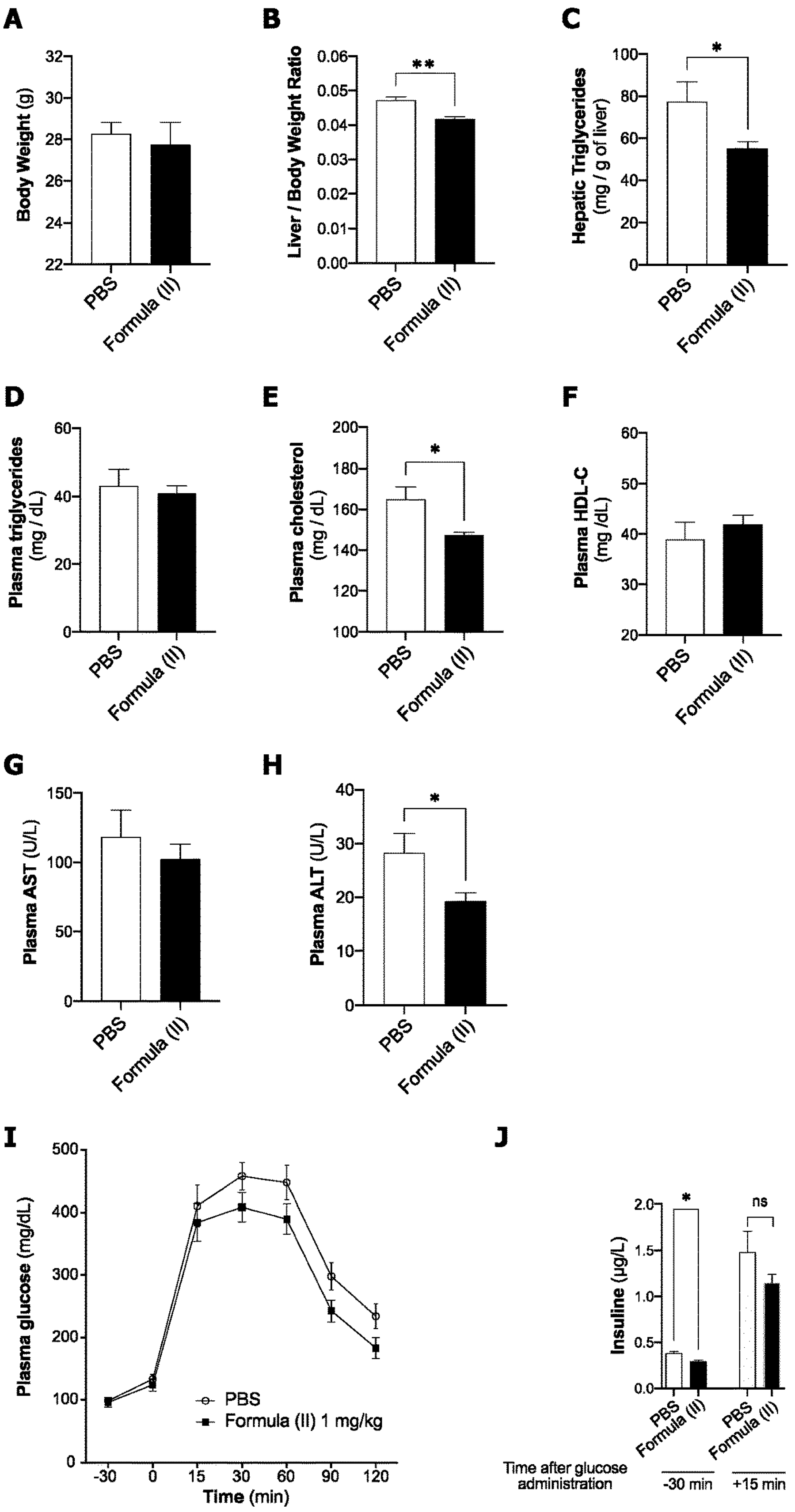
FIG. 12 represents the effect of the peptide of formula (II) in Western diet-induced hepatic steatosis. Mice were daily intraperitoneally administrated for 2 weeks at 1 mg/kg/day with the peptide of formula (I) or PBS (control group). OGTT was realized 10 days after the initiation of peptide administration and the other measurements were performed at the end of treatment period. (A) body weight, (B) liver to body weight ratio, (C) liver triglyceride content, (D-E-F) plasma triglyceride, cholesterol and HDL-C concentrations, (G-H) plasma levels of AST and ALT, (I-J) OGTT and plasma insulin concentrations at −15 and +30 min of OGTT. n=5 mice per group. Data are expressed as mean (i SEM) and are analyzed using unpaired t-test.

The results are presented in FIG. 12. Two-week intraperitoneal injection of the peptide of formula (II) significantly reduced hepatic steatosis, as supported by a decrease of liver/body weight ratio (FIG. 12B, $p<0.01$ versus to PBS) and a reduction of hepatic triglyceride concentration (FIG. 12C, $p<0.05$ versus PBS). The treatment with the peptide of formula (II) had no effect on plasma triglycerides and HDL-cholesterol (HDL-C) levels (FIGS. 12D and 12F) but significantly decrease plasma level of total cholesterol (FIG. 12E, $p<0.05$ versus PBS), indicating a beneficial effect of the peptide of formula (II) in reducing hypercholesterolemia. Treatment with the peptide of formula (II) significantly reduced plasma ALT level (FIG. 12H, $p<0.05$ versus PBS), indicating a potential improvement in liver functions.

Concerning glucose metabolism, the peptide of formula (II) improved oral glucose tolerance (FIG. 121) and decreased basal insulin level (FIG. 12J, $p<0.05$ versus PBS).

The treatment with the peptide of formula (I) demonstrated benefits on NASH-associated steatosis and glucose metabolism. The peptide of formula (I) is therefore a good candidate to treat and reverse hepatic steatosis and to resolve dysregulation of glucose metabolism, particularly in non-alcoholic steatohepatitis (NASH).

Example 13: In Vivo Efficacy of the Peptide of Formula (I) on the Development of NASH Associated Hepatic Fibrosis Materials and Methods Animals.

Wild-type C57B/L6J male mice were purchased from Janvier Labs (Le Genest Saint Isle, France). Mice were caged in animal rooms under specific pathogen free conditions at the animal facility of Rangueil (Anexplo platform, US006, Toulouse, France) with a light/dark schedule of 12 h/12 h. At the initiation of the dietary intervention, all animals were 8 weeks old and were fed ad libitum with a normal chow diet (#V1535 R/M-H, Ssniff, Germany). All animal experimental procedures were conducted in accordance with institutional guidelines on animal experimentation approved by the local ethical committee of animal care and are conformed to the guidelines from Directive 2010/63/EU of the European Parliament on the protection of animals used for scientific purposes or the NIH guideline.

Mouse Model of Diet-Induced NASH Associated Hepatic Fibrosis.

8 weeks old mice were fed for 6 week a choline-deficient, L-amino acid-defined, high-fat diet (CDAHFD #A06071302, Research Diet, USA) consisting of 60 kcal % fat and 0.1% methionine by weight [11]. For the 2 last weeks of the 6-week period, a group of mice were implanted with an osmotic pump containing the peptide of formula (I). Briefly, 200 μL osmotic pump were filled with 10 mg/mL of the peptide of formula (I) in PBS and were implanted subcutaneously into the mice according to the manufacturer's instructions (Alzet®, model pump #2002), to insure the peptide of formula (I) release at an estimated rate of 0.5 μL/h, which corresponds to an estimated amount of delivery of 5 mg of the peptide of formula (I) per kilogram of body weight per day (5 mg/kg BW/day). The control group was composed of mice that underwent the same chirurgical procedure used for osmotic pump implantation (sham-operated mice).

Liver histology. Following the treatment period, mice were fasted overnight, anesthetized by intra-peritoneal injection of ketamine and xylazine hydrochloride then killed by exsanguination. A sample of the main liver lobe was fixed with paraformaldehyde, embedded in paraffin, and sliced into 5 μm sections, then deparaffinized, rehydrated. Fibrosis was assessed by Sirius Red staining. Briefly, sections were incubated for 10 min in 1% Sirius Red (Sigma-Aldrich) dissolved in saturated picric acid and then rinsed with distilled water. Sections were then dehydrated for 15 min with absolute ethanol and incubated with Histoclear® clearing agent (Euromedex, France) before mounting with Distyrene Plasticizer Xylene (DPX) and coverslipping. After staining, slides were scanned with a NanoZoomer 2.0 RS (Hamamatsu, Japan).

Hepatic Hydroxyproline Quantification.

Hepatic hydroxyproline was determined by hydrolizing 80-140 mg liver in a 6N HCl solution, overnight, at 110 degrees Celcius. The samples were diluted in citric-acetate buffer and treated with Chloramine T (Sigma-Aldrich-Aldrich) and 4-(dimethyl)aminobenzaldehyde (Sigma-Aldrich-Aldrich). Absorbance was measured at 550 nm and the results are expressed as micrograms of hepatic hydroxyproline per mg tissue.

Results

Figure 13:
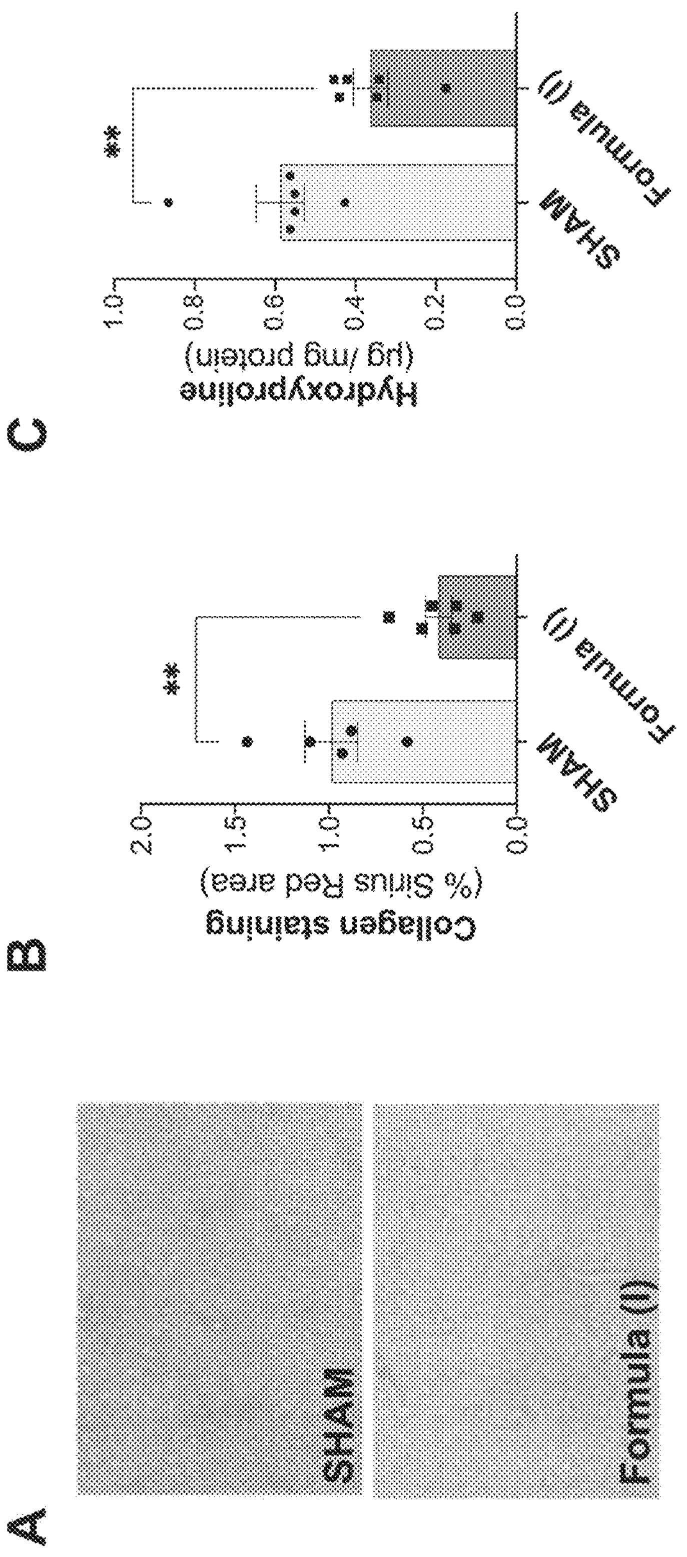
FIG. 13 represents the effect of the peptide of formula (I) in CDAHFD-induced hepatic fibrosis. Peptide of formula (I) was subcutaneously infused for 2-weeks using alzet osmotic pump to insure an estimated amount of delivery of 5 mg of the peptide of formula (I) per kilogram of body weight per day (5 mg/kg BW/day). (A) Representative images of the histological analysis of livers via staining with Sirius Red for mice fed CDAHFD for 6 weeks, with or without (sham) treatment with the peptide of formula (I) for the two last weeks of diet. (B) Quantification of collagen deposition, assessed from the percentage of Sirius Red area. (C) Hydroxyproline quantification (μg/g) from liver tissue of mice fed CDAHFD for 6 weeks, with or without (sham) treatment with the peptide of formula (I) for the two last weeks of diet. Data are expressed as mean (i SEM) and analyzed by Wilcoxon-Mann Whitney test. ** p<0.01. n=6 mice per group

The results are presented in FIG. 13. Two-week subcutaneous infusion of the peptide of formula (I) significantly attenuated the CDAHFD diet-induced increase of hepatic fibrosis in mice. First, histological examination of mouse livers by Sirius Red staining (FIG. 13A, representative images) reveals that mice treated with the peptide of formula (I) had less collagen deposition than non-treated sham-operated mice ($p<0.01$ versus sham-operated mice, FIG. 13B). Second, hepatic fibrosis was evaluated by measuring liver content in the fibrosis marker, hydroxyproline. As reported in FIG. 14C, mice treated with the peptide of formula (I) had more than 35% decrease in the concentration of hydroxyproline content per milligram of liver ($p<0.05$ versus sham-operated mice).

Conclusion

The treatment with the peptide of formula (I) demonstrated benefits on NASH-associated fibrosis. The peptide of formula (I) is therefore a good candidate to treat and reverse hepatic fibrosis, particularly in non-alcoholic steatohepatitis (NASH).

Sequence Listing

| SEQ ID NO: | Description | Sequence |
|---|---|---|
| 1 | Peptide according the invention | RGAGSIREAGGAFGKREQAEEERYFRAQSRE |
| 2 | Scramble peptide, SCR (not according to the invention) | GEAKSYAEKGEARGERGTKGEFRIFKREATD |
| 3 | Signature peptide (not according to the invention) | EAGGAFGK |
| 4 | Signature peptide (not according to the invention) | EAGGAFG |
| 5 | Mature human IF1 | GSDQSENVDRGAGSIREAGGAFGKREQAEEERYFRAQSREQLAALKKHHEEEIVHHKKEIERLQKEIERHKQKIKMLKHDD |

REFERENCES

[1] Martinez et al. 2003. Nature 421; 75-79
[2] Jacquet et al. 2005 Cell Mol Life Sci 62; 2508-2515
[3] Fabre et al. Hepatology 52; 1477-1483
[4] Smith et al. Curr Opin Investig Drugs. 2010 September; 11(9): 989-996
[5] Cabou et al. 2019. Acta Physiol (Oxf).; 226(3):e13268
[6] Martinez et al. 2015. Atherosclerosis. January; 238(1): 89-100
[7] Martinez et al. 2003. Nature 421; 75-79
[8] Iwakiri Y. et al. Trends Pharmacol Sc. 2015 August; 36(8):524-36
[9] Musso, G. et al. 2013. Prog. Lipid Res. 52, 175-191
[10] Min, H. K. et al. 2012. Cell Metab. 15, 665-674
[11] Matsumoto et al. 2013. Int. J. Exp. Path. 94, 93-103
[12] Havel R J et al. (1955) J. Clin. Invest. 34, 1345-1353
[13] Ioannou G. N. Trends in Endocrinology & Metabolism, February 2016, Vol. 27, No. 2
[14] Lichtenstein et al. Cardiovasc Res. 2015 May 1; 106 (2):314-23
[15] Castaing-Berthou A et al. Cell Physiol Biochem. 2017; 42(2):579-593
[16] Farah C et al. Nat Rev Cardiol. 2018; 15(5):292-316.
[17] Corpechot et al. Clin Res Hepatol Gastroenterol. 2012
[18] Pasut, G.; Veronese, F. M. (2012). "State of the art in PEGylation: The great versatility achieved after forty years of research". Journal of Controlled Release. 161 (2): 461-472
[19] Rai, A K (2013) J. Bioenerg. Biomembr. 45, 569e579
[20] Cardouat et al. Biochim Biophys Acta Mol Cell Biol Lipids. 2017 September; 1862(9):832-841

The invention claimed is:

1. A peptide having the amino acid sequence of SEQ ID NO: 1, wherein said peptide is a F1-ATPase activator.

2. The peptide according to claim 1, wherein said peptide has a N-terminal acetylation and/or a C-terminal amidation.

3. The peptide according to claim 1, wherein said peptide is modified by attaching at least one long-lasting molecule at one or more amino acid residues of the peptide.

4. The peptide according to claim 3, wherein said long-lasting molecule is selected from the group consisting of fatty acid, albumin, polyethylene glycol (PEG) and Fc portion of immunoglobulin G.

5. The peptide according to claim 1, wherein said peptide is modified by attaching one palmitic acid at the C-terminus of the peptide.

6. The peptide according to claim 1, wherein said peptide has the formula (I) or (II):

$CH_3CO$-[peptide having the amino acid sequence of SEQ ID NO: 1]-$NH_2$ (I);

$CH_3CO$-[peptide having the amino acid sequence of SEQ ID NO: 1]-K-[palmitoyl]-$NH_2$ (II).

7. A pharmaceutical composition comprising a therapeutically active amount of the peptide according to claim 1 and a pharmaceutically acceptable vehicle or carrier.

8. An isolated sequence encoding the peptide according to claim 1.

9. An isolated vector comprising the nucleotide sequence according to claim 8.

10. An isolated cell comprising the nucleotide sequence according to claim 8.

11. An isolated cell comprising the vector according to claim 9.

12. The peptide according to claim 1, wherein said peptide is modified by attaching at least one long-lasting molecule at one or more amino acid residues at the C-terminus of the peptide.

13. The peptide according to claim 3, wherein said long-lasting molecule is a fatty acid.

* * * * *